(12) United States Patent
Cortright et al.

(10) Patent No.: US 8,231,857 B2
(45) Date of Patent: Jul. 31, 2012

(54) CATALYSTS AND METHODS FOR REFORMING OXYGENATED COMPOUNDS

(75) Inventors: Randy D. Cortright, Madison, WI (US); Nicholas W. Vollendorf, New Berlin, WI (US); Charles C. Hornemann, Madison, WI (US); Shawn P. McMahon, Madison, WI (US)

(73) Assignee: Virent, Inc., Madison, WI (US)

( * ) Notice: Subject to any disclaimer, the term of this patent is extended or adjusted under 35 U.S.C. 154(b) by 414 days.

(21) Appl. No.: 12/158,635

(22) PCT Filed: Dec. 18, 2006

(86) PCT No.: PCT/US2006/048030
§ 371 (c)(1),
(2), (4) Date: Oct. 27, 2008

(87) PCT Pub. No.: WO2007/075476
PCT Pub. Date: Jul. 5, 2007

(65) Prior Publication Data
US 2009/0211942 A1    Aug. 27, 2009

Related U.S. Application Data

(60) Provisional application No. 60/752,485, filed on Dec. 21, 2005.

(51) Int. Cl.
*C01B 3/22* (2006.01)
*B01J 21/18* (2006.01)
*C07C 1/20* (2006.01)

(52) U.S. Cl. .............. 423/648.1; 252/373; 502/185; 585/733

(58) Field of Classification Search ............... 502/303, 502/304, 185; 423/648.1, 650, 651, 652; 252/373; 585/733
See application file for complete search history.

(56) References Cited

U.S. PATENT DOCUMENTS

| | | | |
|---|---|---|---|
| 2,965,679 | A | 12/1960 | Conradin et al. |
| 3,894,107 | A | 7/1975 | Butter et al. |
| 4,013,734 | A | 3/1977 | Kim |
| 4,223,001 | A | 9/1980 | Novotny et al. |
| 4,380,679 | A | 4/1983 | Arena |

(Continued)

FOREIGN PATENT DOCUMENTS

CA    1201080 A    2/1986

(Continued)

OTHER PUBLICATIONS

Gayubo et al., "Transformation of Oxygenate Components of Biomass Pyrolsis Oil on a HZSM-5 Zeolite. I. Alcohols and Phenols," Ind. Eng. Chem Res. 2004, 43:2610-2618.

(Continued)

*Primary Examiner* — Wayne Langel
(74) *Attorney, Agent, or Firm* — Quarles & Brady LLP

(57) ABSTRACT

Disclosed are catalysts and methods that can reform aqueous solutions of oxygenated compounds such as ethylene glycol, glycerol, sugar alcohols, and sugars to generate products such as hydrogen and alkanes. In some embodiments, aqueous solutions containing at least 20 wt % of the oxygenated compounds can be reformed over a catalyst comprising a Group VIII transition metal and a Group VIIB transition metal, preferably supported on an activated carbon-supported catalyst. In other embodiments, catalysts are provided for the production of hydrogen or alkanes at reaction temperatures less than 300° C.

18 Claims, 5 Drawing Sheets

U.S. PATENT DOCUMENTS

| | | |
|---|---|---|
| 4,380,680 A | 4/1983 | Arena |
| 4,382,150 A | 5/1983 | Arena |
| 4,401,823 A | 8/1983 | Arena |
| 4,456,779 A | 6/1984 | Owen et al. |
| 4,476,331 A | 10/1984 | Dubeck et al. |
| 4,487,980 A | 12/1984 | Arena |
| 4,496,780 A | 1/1985 | Arena |
| 4,503,274 A | 3/1985 | Arena |
| 4,541,836 A | 9/1985 | Derderian |
| 4,543,435 A | 9/1985 | Gould et al. |
| 4,554,260 A | 11/1985 | Pieters et al. |
| 4,642,394 A | 2/1987 | Che |
| 4,717,465 A | 1/1988 | Chen et al. |
| 4,828,812 A | 5/1989 | McCullen et al. |
| 4,885,421 A | 12/1989 | Harandi et al. |
| 4,919,896 A | 4/1990 | Harandi et al. |
| 4,935,568 A | 6/1990 | Harandi et al. |
| 5,001,292 A | 3/1991 | Harandi et al. |
| 5,006,131 A | 4/1991 | Karafian et al. |
| 5,019,135 A | 5/1991 | Sealock, Jr. et al. |
| 5,026,927 A | 6/1991 | Andrews et al. |
| 5,095,159 A | 3/1992 | Harandi et al. |
| 5,105,044 A | 4/1992 | Han et al. |
| 5,130,101 A | 7/1992 | Harandi et al. |
| 5,139,002 A | 8/1992 | Lynch et al. |
| 5,149,884 A | 9/1992 | Brenner et al. |
| 5,177,279 A | 1/1993 | Harandi |
| 5,214,219 A | 5/1993 | Casale et al. |
| 5,238,898 A | 8/1993 | Han et al. |
| 5,306,847 A | 4/1994 | Gehrer et al. |
| 5,326,912 A | 7/1994 | Gubitosa et al. |
| 5,344,849 A | 9/1994 | Ayasse |
| 5,354,914 A | 10/1994 | Gubitosa et al. |
| 5,496,786 A | 3/1996 | Gubitosa et al. |
| 5,504,259 A | 4/1996 | Diebold et al. |
| 5,543,379 A | 8/1996 | Gubitosa et al. |
| 5,578,647 A | 11/1996 | Li et al. |
| 5,600,028 A | 2/1997 | Gubitosa et al. |
| 5,616,154 A | 4/1997 | Elliott et al. |
| 5,616,817 A | 4/1997 | Schuster et al. |
| 5,635,145 A | 6/1997 | Den Hartog et al. |
| 5,651,953 A | 7/1997 | Yokoyama et al. |
| 5,660,602 A | 8/1997 | Collier, Jr. et al. |
| 5,666,923 A | 9/1997 | Collier, Jr. et al. |
| 5,787,864 A | 8/1998 | Collier, Jr. et al. |
| 5,817,589 A | 10/1998 | de Agudelo et al. |
| 5,861,137 A | 1/1999 | Edlund |
| 5,959,167 A | 9/1999 | Shabtai et al. |
| 6,054,041 A | 4/2000 | Ellis et al. |
| 6,059,995 A | 5/2000 | Topsoe et al. |
| 6,152,975 A | 11/2000 | Elliott et al. |
| 6,171,992 B1 | 1/2001 | Autenrieth et al. |
| 6,172,272 B1 | 1/2001 | Shabtai et al. |
| 6,207,132 B1 | 3/2001 | Lin et al. |
| 6,235,797 B1 | 5/2001 | Elliot et al. |
| RE37,329 E | 8/2001 | Gubitosa et al. |
| 6,280,701 B1 | 8/2001 | Autenrieth et al. |
| 6,291,725 B1 | 9/2001 | Chopade et al. |
| 6,323,383 B1 | 11/2001 | Tsuchida et al. |
| 6,361,757 B1 | 3/2002 | Shikada et al. |
| 6,372,680 B1 | 4/2002 | Wu et al. |
| 6,373,680 B1 | 4/2002 | Riskin |
| 6,387,554 B1 | 5/2002 | Verykios |
| 6,397,790 B1 | 6/2002 | Collier, Jr. |
| 6,413,449 B1 | 7/2002 | Wieland et al. |
| 6,429,167 B1 | 8/2002 | Maeno et al. |
| 6,440,895 B1 | 8/2002 | Tonkovich et al. |
| 6,479,428 B1 | 11/2002 | Tonkovich et al. |
| 6,479,713 B1 | 11/2002 | Werpy et al. |
| 6,486,366 B1 | 11/2002 | Ostgard et al. |
| 6,508,209 B1 | 1/2003 | Collier, Jr. |
| 6,570,043 B2 | 5/2003 | Elliott et al. |
| 6,582,667 B1 | 6/2003 | Ogata et al. |
| 6,607,707 B2 | 8/2003 | Reichman et al. |
| 6,670,300 B2 | 12/2003 | Werpy et al. |
| 6,677,385 B2 | 1/2004 | Werpy et al. |
| 6,739,125 B1 | 5/2004 | Mulligan |
| 6,749,828 B1 | 6/2004 | Fukunaga |
| 6,762,149 B2 | 7/2004 | Tonkovich et al. |
| 6,765,101 B1 | 7/2004 | Bhasin et al. |
| 6,841,085 B2 | 1/2005 | Werpy et al. |
| 6,964,757 B2 * | 11/2005 | Cortright et al. ............ 423/648.1 |
| 6,964,758 B2 | 11/2005 | Cortright et al. |
| 6,969,506 B2 | 11/2005 | Tonkovich et al. |
| 6,982,328 B2 | 1/2006 | Werpy et al. |
| 7,022,824 B2 | 4/2006 | Vanoppen et al. |
| 7,038,094 B2 | 5/2006 | Werpy et al. |
| 7,070,745 B2 | 7/2006 | Van Der Meer et al. |
| 7,112,312 B2 | 9/2006 | Chou |
| 7,186,668 B2 | 3/2007 | Werpy et al. |
| 7,199,250 B2 | 4/2007 | Werpy et al. |
| 7,232,935 B2 | 6/2007 | Jakkula et al. |
| 7,273,957 B2 | 9/2007 | Bakshi et al. |
| 7,288,685 B2 | 10/2007 | Marker |
| 7,297,814 B2 | 11/2007 | Yada et al. |
| 7,355,083 B2 | 4/2008 | Tuck et al. |
| 7,520,909 B2 | 4/2009 | Rogers |
| 7,578,927 B2 | 8/2009 | Marker et al. |
| 7,615,652 B2 | 11/2009 | Holladay et al. |
| 7,618,612 B2 | 11/2009 | Cortright et al. |
| 7,649,099 B2 | 1/2010 | Holladay et al. |
| 7,652,131 B2 | 1/2010 | Werpy et al. |
| 7,663,004 B2 | 2/2010 | Suppes et al. |
| 7,674,916 B2 | 3/2010 | Werpy et al. |
| 7,692,001 B2 | 4/2010 | Holcomb |
| 7,767,867 B2 | 8/2010 | Cortright |
| 2003/0099593 A1 | 5/2003 | Cortright |
| 2003/0100807 A1 | 5/2003 | Shabtai et al. |
| 2003/0115792 A1 | 6/2003 | Shabtai et al. |
| 2003/0170171 A1 * | 9/2003 | Cortright et al. ............ 423/648.1 |
| 2003/0175561 A1 | 9/2003 | Lightner |
| 2003/0220531 A1 | 11/2003 | Cortright |
| 2005/0064560 A1 | 3/2005 | Werpy et al. |
| 2005/0203195 A1 | 9/2005 | Wang et al. |
| 2005/0244329 A1 | 11/2005 | Casanave et al. |
| 2006/0013759 A1 | 1/2006 | Jiang et al. |
| 2006/0024539 A1 | 2/2006 | Dumesic et al. |
| 2007/0123739 A1 | 5/2007 | Crabtree et al. |
| 2007/0135301 A1 | 6/2007 | Holcomb, Jr. |
| 2008/0216391 A1 | 9/2008 | Cortright et al. |
| 2008/0300434 A1 | 12/2008 | Cortright et al. |
| 2008/0300435 A1 | 12/2008 | Cortright et al. |
| 2009/0211942 A1 | 8/2009 | Cortright et al. |
| 2010/0008840 A1 * | 1/2010 | Zhong et al. ................. 423/247 |
| 2010/0076233 A1 | 3/2010 | Cortright et al. |

FOREIGN PATENT DOCUMENTS

| | | |
|---|---|---|
| EP | 0204354 A1 | 12/1986 |
| EP | 0323663 B2 | 9/1994 |
| EP | 1454671 A1 | 9/2004 |
| EP | 1724325 A1 | 11/2006 |
| FO | 2857003 | 1/2005 |
| GB | 2097390 A | 11/1982 |
| JP | 2004344721 A | 12/2004 |
| WO | 9429013 A1 | 12/1994 |
| WO | 9910450 A1 | 3/1999 |
| WO | 9961369 A1 | 12/1999 |
| WO | 0200341 A2 | 1/2002 |
| WO | WO 03004581 A1 | 6/2003 |
| WO | 2004039918 A2 | 5/2004 |
| WO | 2004052813 A1 | 6/2004 |
| WO | 2005037423 A1 | 4/2005 |
| WO | 2006100584 A2 | 9/2006 |
| WO | 20060119357 A2 | 11/2006 |
| WO | 2007027832 A2 | 3/2007 |
| WO | 2007053705 A2 | 5/2007 |
| WO | 2007075476 A2 | 7/2007 |
| WO | 2007099161 A1 | 9/2007 |
| WO | 2008109877 A1 | 9/2008 |

OTHER PUBLICATIONS

Gayubo et al., "Transformation of Oxygenate Components of Biomass Pyrolsis Oil on a HZSM-5 Zeolite. II. Aldehydes, Ketones, and Acids," Ind. Eng. Chem Res. 2004, 43:2619-2626.

Agar, et al., "Abstract 2254—Influence of the Liquid Phase Physical Properties on Unsteady-State Hydrodynamics in Periodically Operated Trickle-Bed Reactors," European Congress of Chemical Engineering—6, Copenhagen Sep. 2007.
Badger, "Ethanol From Cellulose: A General Review," 2002 J. Janick and A. Whipkey (eds.), Trends in New Crops and New Uses, ASHA Press, Alexandria, VA, pp. 17-21.
Bardin, et al., "Acidity of Keggin-Type Heteropolycompounds Evaluated by Catalytic Probe Reactions, Sorption Microcalorimetry, and Density Functional Quantum Chemical Calculations" 1998 J. Phys. Chem. B 102:10817-10825.
Barrett, et al., "Single-Reactor Process for Sequential Aldol-Condensation and Hydrogenation of Biomass-Derived Compounds in Water," 2006 Applied Catalysis B: Environmental 66:111-118.
Brown, et al., "Carbon-Halogen Bond Scission and Rearrangement of Beta-Halohydrins on the Rh(111) Surface" 1994 J. Phys. Chem. 98:12737-12745.
Chaminand, et al., "Glycerol Hydrogenolysis on Heterogeneous Catalysts", 2004 Green Chemistry 6:359-361.
Chen, et al., "Liquid Fuel From Carbohydrates," Aug. 1986 Chemtech pp. 506-509.
Chiu, et al., "Distribution of Methanol and Catalysts Between Biodiesel and Glycerin Phases" 2005 AIChE Journal 51:1274-1278.
Chiu, et al., "Removal of Residual Catalyst from Simulated Biodiesel's Crude Glycerol for Glycerol Hydrogenolysis to Propylene Glycol" 2006 Ind. Eng. Chem. Res. 45:791-795.
Corma, et al., "Processing Biomass-Derived Oxygenates in the Oil Refinery: Catalytic Cracking (FCC) Reaction Pathways and Role of Catalyst," 2007 Journal of Catalysis 247:307-327.
Cortright, et al., "Hydrogen from Catalytic Reforming of Biomass-Derived Hydrocarbons in Liquid Water" 2002 Nature 418:964-967.
Crabtree, et. al., "Novel Catalysis for Glycol Manufacture", 2001.
Dasari, et al., "Low-Pressure Hydrogenolysis of Glycerol to Propylene Glycol" 2005 Applied Catalysis A: General 281:225-231.
Dass, et al., "A Comparative Study of the Conversion of Ethanol and of Ethylene Over the 'Mobil' Zeolite Catalyst, H-ZSM-5. An application of the Benzene Sequestration Test," 1989 Can. J. Chem. 67:1732-1734.
Davda, et al., "A Review of Catalytic Issues and Process Conditions for Renewable Hydrogen and Alkanes by Aqueous-Phase Reforming of Oxygenated Hydrocarbons Over Supported Metal Catalysts" 2005 Applied Catalysis B: Environmental 56:171-186.
Davda, et al., "Aqueous-Phase Reforming of Ethylene Glycol on Silica-Supported Metal Catalysts" 2003 Applied Catalysis B: Environmental 43:13-26.
Davda, et al., "Catalytic Reforming of Oxygenated Hydrocarbons for Hydrogen with Low Levels of Carbon Monoxide" 2003 Angew. Chem. Int. Ed., 42:4068-4071.
Davda, et al., "Renewable Hydrogen by Aqueous-Phase Reforming of Glucose" 2004 Chem. Commun., pp. 36-37.
Dos Santos, et al., "Performance of RuSn Catalysts Supported on Different Oxides in the Selective Hydrogenation of Dimethyl Adipate," 2005 Catalysis Today 107-108:250-257.
Elliott, et al., "Chemical Processing in High-Pressure Aqueous Environments. 7. Process Development for Catalytic Gasification of Wet Biomass Feedstocks" 2004 Ind. Eng. Chem. Res. 43:1999-2004.
Elliott, et al.. "Chemical Processing in High-Pressure Aqueous Environments. 6. Demonstration of Catalytic Gasification for Chemical Manufacturing Wastewater Cleanup in Industrial Plants" 1999 Ind. Eng. Chem. Res. 38:879-883.
Elliott, et al., "Liquid Fuels by Low-Severity Hydrotreating of Biocrude," 1996 Developments in Thermochemical Biomass Conversion 1:611-621.
Fraser, "Roadmap for Cellulosic Ethanol Production," U.S. Department of Energy, Jun. 2006.
Fukuoka, et al., "Catalytic Conversion of Cellulose into Sugar Alcohols," 2006 Angew. Chem. Int. Ed. 45:5161-5163.
Greer, "Creating Cellulosic Ethanol: Spinning Straw into Fuel," May 2005 eNews Bulletin.
Huber, et al., "Production of Liquid Alkanes by Aqueous-Phase Processing of Biomass-Derived Carbohydrates" 2005 Science 308:1446-1450.
Huber, et al., "Raney Ni-Sn Catalyst for H2 Production from Biomass-Derived Hydrocarbons," 2003 Science 300:2075-2077.
Huber, et al., "Renewable Alkanes by Aqueous-Phase Reforming of Biomass-Derived Oxygenates" 2004 Angew. Chem. Int. Ed., 43:1549-1551.
Huber, et al., "Synthesis of Transportation Fuels from Biomass: Chemistry, Catalysts, and Engineering" 2006 Chem. Rev. 106:4044-4098.
Kawai, et al., "Production of Hydrogen and Hydrocarbon From Cellulose and Water" 1981 Chemistry Letters pp. 1185-1188.
Kluson, et al. "Selective Hydrogenation over Ruthenium Catalysts" 1995 Applied Catalysis A: General 128:13-31.
Makarova, et al., "Dehydration of n-Butanol on Zeolite H-ZSM-5 and Amorphous Aluminosilicate: Detailed Mechanistic Study and the Effect of Pore Confinement" 1994 Journal of Catalysis 149:36-51.
Minowa, et al., "Hydrogen Production from Cellulose in Hot Compressed Water Using Reduced Nickel Catalyst: Product Distribution at Different Reaction Temperatures" 1998 J. of Chem. Eng. of Japan 31:488-491.
Minowa, et al., "Hydrogen Production from Wet Cellulose by Low Temperature Gasification Using a Reduced Nickel Catalyst" 1995 Chemistry Letters pp. 937-938.
Miyazawa, et al., "Glycerol Conversion in the Aqueous Solution under Hydrogen over Ru/C + an Ion-Exchange Resin and Its Reaction Mechanism" 2006 J. of Catalysis 240:213-221.
Nelson, et al., "Application of Direct Thermal Liquefaction for the Conversion of Cellulosic Biomass" 1984 Ind. Eng. Chem. Prod. Res. Dev. 23:471-475.
Oregon Cellulose-Ethanol Study, Appendix B Overview of Cellulose-Ethanol Production Technology 1998 pp. 57-60.
Roman-Leshkov, et al., "Production of Dimethylfuran for Liquid Fuels from Biomass-Derived Carbohydrates" 2007 Nature 447:982-986.
Rostrup-Nielsen, "Conversion of Hydrocarbons and Alcohols for Fuel Cells" 2001 Phys. Chem. Chern. Phys. 3:283-288.
Shabaker, et al., "Aqueous-Phase Reforming of Ethylene Glycol over Supported Platinum Catalysts" 2003 Catal. Lett., vol. 88, Nos. 1-2.
Shabaker, et al., "Aqueous-Phase Reforming of Methanol and Ethylene Glycol Over Alumina-Supported Platinum Catalysts" 2003 Journal of Catalysis 215:344-352.
Shabaker, et al., "Aqueous-Phase Reforming of Oxygenated Hydrocarbons Over Sn-Modified Ni Catalysts" 2004 Journal of Catalysis 222:180-191.
Shabaker, et al., "Sn-modified Ni Catalysts for Aqueous-Phase Reforming: Characterization and Deactivation Studies" 2005 Journal of Catalysis 231:67-76.
Shabaker, et al., "Kinetics of Aqueous-Phase Reforming of Oxygenated Hydrocarbons: Pt/Al2O3 and Sn-Modified Ni Catalysts" 2004 Ind. Eng, Chem. Res., 43:3105-3112.
Silva, et al., "Role of Catalyst Preparation on Determining Selective Sites for Hydrogenation of Dimethyl Adipate Over RuSn/Al2O3," 2006 J. of Molecular Catalysis A: Chemical 253:62-69.
Tsuchida, et al., "Direct Synthesis of n-Butanol from Ethanol over Nonstoichiometric Hydroxyapatite" 2006 Ind. Eng. Chem. Res. 45:8634-8642.
Wang, et al., "Catalytic Steam Reforming of Biomass-Derived Oxygenates: Acetic Acid and Hydroxyacetaldehyde" 1996 Applied Catalysis A: General 143:245-270.
Werpy, et al., "Top Value Added Chemicals from Biomass, vol. 1: Results of Screening for Potential Candidates from Sugars and Synthesis Gas," 2004 National Renewable Energy Laboratory, Pacific Northwest National Laboratory.
United States Patent and Trademark Office, Office Action, U.S. Appl. No. 11/961,280, Mar. 9, 2011.
Applicant, Response to Restriction Requirement (Mar. 9, 2011), U.S. Appl. No. 11/961,280, Apr. 11, 2011.
Yoshida et al., "Gasification of Cellulose, Xylan, and Lignin Mixtures in Supercritical Water" 2001 Ind. Eng. Chem. Res. 40:5469-5474.
United States Patent and Trademark Office, Office Action Summary and Detailed Action, U.S. Appl. No. 11/800,671, Dec. 26, 2008.
Applicant, Response to Restriction Requirement, U.S. Appl. No. 11/800,671, Jan. 26, 2009.

United States Patent and Trademark Office, Office Action Summary and Detailed Action, U.S. Appl. No. 11/800,671, Apr. 8, 2009.
Applicant, Response to Non-Final Office Action, U.S. Appl. No. 11/800,671, Aug. 10, 2009.
United States Patent and Trademark Office, Issue Notification, U.S. Appl. No. 11/800,671, Aug. 3, 2010.
United States Patent and Trademark Office, Office Action Summary and Detailed Action, U.S. Appl. No. 12/044,837, Aug. 12, 2010.
United States Patent and Trademark Office, Interview Summary, U.S. Appl. No. 12/044,837, Oct. 28, 2010.
Applicant, Response to Non-Final Office Action, U.S. Appl. No. 12/044,837, Nov. 12, 2010.
Applicant, Supplemental Response to Non-Final Office Action, U.S. Appl. No. 12/044,837, Jan. 5, 2011.
United States Patent and Trademark Office, Office Action Summary and Detailed Action, U.S. Appl. No. 12/044,908, Aug. 12, 2010.
United States Patent and Trademark Office, Interview Summary, U.S. Appl. No. 12/044,908, Oct. 29, 2010.
Applicant, Response to Non-Final Office Action, U.S. Appl. No. 12/044,908, Nov. 12, 2010.
Applicant, Supplemental Response to Non-Final Office Action, U.S. Appl. No. 12/044,908, Jan. 5, 2011.
United States Patent and Trademark Office, Office Action Summary and Detailed Action, U.S. Appl. No. 12/044,876, Aug. 16, 2010.
United States Patent and Trademark Office, Interview Summary, U.S. Appl. No. 12/044,876, Oct. 28, 2010.
Applicant, Response to Non-Final Office Action, U.S. Appl. No. 12/044,876, Nov. 12, 2010.
Applicant, Supplemental Response to Non-Final Office Action, U.S. Appl. No. 12/044,876, Jan. 5, 2011.
United States Patent and Trademark Office, Office Action Summary and Detailed Action, U.S. Appl. No. 12/834,306, Sep. 17, 2010.
Applicant, Response to Non-Final Office Action, U.S. Appl. No. 12/834,306, Dec. 15, 2010.
PCT International Search Report, Application No. PCT/US2007/011062, Sep. 16, 2008.
PCT International Preliminary Report on Patentability, Application No. PCT/US2007/011062, Nov. 11, 2008.
European Patent Office, Examination Report, Application No. 07870663.7, Oct. 22, 2010.
Ukraine Patent Office, Office Action, Application No. a 2008 12327, 2010.
Republic of South Africa, Letters Patent, Patent No. 2008/09194, Dec. 30, 2009.
Intellectual Property Office of New Zealand, Examination Report, Application No. 572113, Jun. 4, 2010.
PCT International Search Report, Application No. PCT/US2006/048030, Dec. 27, 2007.
PCT Written Opinion, Application No. PCT/US2006/048030, Jun. 21, 2008.
State Intellectual Property Office of the People's Republic of China, First Office Action (Translation), Application No. 200680048598.5, Jun. 11, 2010.

Applicant, Response to State Intellectual Property Office of the People's Republic of China First Office Action, Application No. 200680048598.5, Oct. 21, 2010 [includes AFD China Intellectual Property Law Office Oct. 22, 2010 letter; Quarles & Brady Oct. 13, 2010 letter; English version of Amended Claims].
State Intellectual Property Office of the People's Republic of China, Second Office Action (Translation), Application No. 200680048598.5, Jan. 10, 2011.
Patent Office of the Russian Federation, Office Action (Inquiry) of the State Examination, Applicaiton No. 2008127066, Nov. 15, 2010.
Ukraine Patent Office, Office Action, Application No. a 2008 09306, 2010.
Applicant, Response to Ukraine Patent Office Office Action, Application No. a 2008 09306, Dec. 2010 [includes Papula-Nevinpat Dec. 8, 2010 letter].
Ukraine Patent Office, Office Action, Application No. a 2008 09306, Jan. 2011.
Intellectual Property Office of New Zealand, Examination Report, Application No. 569246, Mar. 2, 2010.
PCT International Search Report and Written Opinion, Application No. PCT/US2007/088417, Dec. 2, 2008.
PCT International Preliminary Report on Patentability, Application No. PCT/US2007/088417, Jun. 24, 2009.
Intellectual Property Office of New Zealand, Examination Report, Application No. 577547, Sep. 17, 2010.
Republic of South Africa, Letters Patent, Patent No. 2009/04056, Apr. 28, 2010.
PCT International Search Report, Application No. PCT/US2008/056330, Jul. 10, 2008.
PCT International Preliminary Report on Patentability, PCT/US2008/056330, Sep. 8, 2009.
European Patent Office, Communication, Application No. 08731758.2, Apr. 2, 2009.
Applicant, Response to European Patent Office Apr. 2, 2009 Communication, Application No. 08731758.2, May 1, 2009.
European Patent Office, Communication, Application No. 08731758.2, Mar. 25, 2010.
Applicant, Response to European Patent Office Mar. 25, 2010, Communication, Application No. 08731758.2, Oct. 1, 2010.
Intellectual Property Office of New Zealand, Examination Report, Application No. 579525, Sep. 29, 2010.
Republic of South Africa, Letters Patent, Patent No. 2009/05916, Apr. 28, 2010.
PCT International Search Report and Written Opinion, Application No. PCT/US2010/040644, Feb. 4, 2011.
Examiner's Report on Austrailian pat. app. No. 2006332008 mailed May 9, 2012.
Applicant's Response on Australian pat. app. No. 2006332008 mailed May 4, 2012.
Office action for Japanese pat. app. No. 2008-547362 received May 16, 2012.
Preliminary Opinion for Ukrainian pat. app. No. 2008-09306 mailed May 8, 2012.

* cited by examiner

CATALYSTS AND METHODS FOR REFORMING OXYGENATED COMPOUNDS

This application is a 371 of PCT/US2006/048030 filed Dec. 18, 2006, which claims the benefit of provisional application SN 60/752,485 filed Dec. 21, 2005.

FEDERALLY SPONSORED RESEARCH OR DEVELOPMENT

This invention was made with United States government support awarded by DOC NIST ATP Grant No 70NANB3H3014 and DOE Grant No. DE-FG36-04GO14258. The United States has certain rights in this invention.

TECHNICAL FIELD

The present invention is directed to catalysts and methods for reforming oxygenated compounds, including biomass-derived compounds, to form products such as hydrogen or alkanes via reforming processes, such as aqueous-phase reforming. Catalysts and processes disclosed herein can be used, for example, to reform aqueous solutions of glycerol, sugar alcohols, sugars or polyols such as ethylene glycol and propylene glycol, as well as hydrocarboxylic acids.

BACKGROUND

There are finite quantities of nonrenewable fossil fuels such as crude oil and natural gas that are currently being utilized to generate energy. Biomass (plant-derived material) is one the most important renewable energy resources. The conversion of biomass to fuels, chemicals, materials and power reduces the dependence on foreign oil and natural gas. Currently, biomass provides the only renewable alternative for liquid transportation fuel. Biomass use strengthens rural economies, decreases America's dependence on imported oil, reduces air and water pollution, and reduces greenhouse gas emissions.

A key challenge for promoting and sustaining the vitality and growth of the industrial sector is to develop efficient and environmentally benign technologies for generating fuels, such as hydrogen, from renewable resources. The generation of energy from renewable resources such as biomass, reduces the net rate of production of carbon dioxide, an important greenhouse gas that contributes to global warming. This is because the biomass itself consumes carbon dioxide during its life cycle.

Aqueous-Phase Reforming (APR) is a catalytic reforming process that generates hydrogen-rich fuel gas from oxygenated compounds derived from biomass (glycerol, sugars, sugar alcohols). The resulting fuel gas may be used as a fuel source for electricity generation via PEM fuel cells, solid-oxide fuel cells, internal combustion engines genset, or gas turbine genset. APR processes may generate light hydrocarbons (e.g. methane, ethane, propane, butane, propane, and hexane) and/or hydrogen by the reaction of oxygenated compounds with liquid water at low temperatures (e.g., less than 300° C.). The key breakthrough of the APR process is that the reforming can be done in the liquid phase. The APR process can occur at temperatures (e.g., 150° C. to 270° C.) where the water-gas shift reaction is favorable, making it possible to generate hydrogen with low amounts of CO in a single chemical reactor. Advantages of the APR process include: (i) performing the reaction at pressures (typically 15 to 50 bar) where the hydrogen-rich effluent can be effectively purified; (ii) generation of hydrogen-rich fuel gas at low temperatures without the need to volatilize water, which represents a major energy saving; (iii) operation at temperatures where the water-gas shift reaction is favorable, making it possible to generate high quality fuel gas with low amounts of CO in a single chemical reactor, (iv) operation at temperatures which minimize undesirable decomposition reactions typically encountered when carbohydrates are heated to elevated temperatures, and (v) utilization of agricultural derived feedstocks found in the United States.

The APR process takes advantage of the thermodynamic properties of oxygenated compounds containing a C:O stoichiometry of 1:1 to generate hydrogen from these oxygenated compound at relatively low temperatures in a single reaction step (see FIG. 1), in contrast to certain multi-reactor systems used for producing hydrogen via steam reforming of hydrocarbons. FIG. 1 was constructed from thermodynamic data obtained from Chemical Properties Handbook, C. L. Yaws, McGraw Hill, 1999.

Reaction conditions for producing hydrogen from hydrocarbons can be dictated by the thermodynamics for the steam reforming of the alkanes to form CO and $H_2$ (reaction 1) and the water-gas shift reaction to form $CO_2$ and $H_2$ from CO (reaction 2).

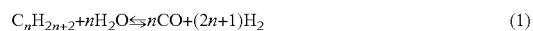

(1)

(2)

FIG. 1 shows changes in the standard Gibbs free energy ($\Delta G^\circ/RT$) associated with reaction 1 for a series of alkanes ($CH_4$, $C_2H_6$, $C_3H_8$, $C_6H_{14}$), normalized per mole of CO produced. The steam reforming of alkanes is thermodynamically favorable (i.e., negative values of $\Delta G^\circ/RT$) at temperatures higher than about 675 K. Oxygenated hydrocarbons having a C:O ratio of 1:1 produce CO and $H_2$ according to reaction 3.

(3)

Relevant oxygenated hydrocarbons having a C:O ratio of 1:1 include methanol ($CH_3OH$), ethylene glycol ($C_2H_4(OH)_2$), glycerol ($C_3H_5(OH)_3$), and sorbitol ($C_6H_8(OH)_6$). On FIG. 1, dotted lines show values of ln(P) for the vapor pressures versus temperature of $CH_3(OH)$, $C_2H_4(OH)_2$, $C_3H_5(OH)_3$, and $C_6H_8(OH)_6$ (pressure in units of atm). FIG. 1 shows that steam reforming of these oxygenated hydrocarbons to produce CO and $H_2$ may be thermodynamically favorable at significantly lower temperatures than those required for alkanes with similar numbers of carbon atoms. Accordingly, the steam reforming of oxygenated hydrocarbons having a C:O ratio of 1:1 would offer a low-temperature route for the formation of CO and $H_2$. FIG. 1 also shows that the value of $\Delta G^\circ/RT$ for water-gas shift of CO to $CO_2$ and $H_2$ is more favorable at lower temperatures. Therefore, it is possible to produce $H_2$ and $CO_2$ from steam reforming of oxygenated compounds utilizing a single-step catalytic process, since the water-gas shift reaction is favorable at the same low temperatures where steam reforming of carbohydrates is possible.

While FIG. 1 shows that the conversion of oxygenated compounds in the presence of water to $H_2$ and $CO_2$ is highly favorable at this low temperature, the subsequent reaction of $H_2$ and $CO_2$ to form alkanes ($C_nH_{2n+2}$) and water is also highly favorable at low temperatures. For example, the equilibrium constant at 500 K for the conversion of $CO_2$ and $H_2$ to methane (reaction 4) is of the order of 1010 per mole of $CO_2$.

(4)

The reforming reaction can be optimized not only to yield hydrogen, but to yield hydrocarbons. For example, the complete reforming of sorbitol yields 13 moles of hydrogen for every 6 moles of CO$_2$ produced:

$$C_6H_{14}O_6 + 6H_2O \rightarrow 6CO_2 + 13H_2 \qquad (5)$$

However, the more thermodynamically favored reaction consumes the hydrogen to yield a mixture of water and hydrocarbons:

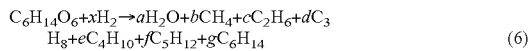

$$C_6H_{14}O_6 + xH_2 \rightarrow aH_2O + bCH_4 + cC_2H_6 + dC_3H_8 + eC_4H_{10} + fC_5H_{12} + gC_6H_{14} \qquad (6)$$

Referring to FIG. 2, the individual reactions for the production of methane, ethane, and hexane are all thermodynamically favored (i.e., $\Delta G^\circ/RT<0$) across the entire temperature range presented in the graph. Moreover, production of these hydrocarbons is more favorable than the generation of hydrogen from the reaction of water with sorbitol. The thermodynamics for the formation of propane, butane, and pentane fit smoothly within the homologous series (between ethane and hexane), but these traces have been omitted from FIG. 2 for clarity. Thus, as described in full below, the present reaction can be optimized to yield a product mixture comprising almost exclusively hydrocarbons rather than hydrogen. FIG. 2 was constructed from thermodynamic data obtained from Chemical Properties Handbook, C. L. Yaws, McGraw Hill, 1999.

U.S. Pat. No. 6,699,457 to Cortright et al., as well as published U.S. patent application US 2005/0207971 A1 with Ser. No. 11/124,717 and filed May 9, 2005, which are incorporated herein by reference, disclose a method of producing hydrogen from oxygenated hydrocarbon reactants, including examples showing conversion of feedstocks comprising up to 10% glycerol, glucose, or sorbitol to hydrogen. The method can take place in the vapor phase or in the condensed liquid phase. The method can include the steps of reacting water and a water-soluble oxygenated hydrocarbon having at least two carbon atoms, in the presence of a metal-containing catalyst. The catalyst contains a metal selected from the group consisting of Group VIII transitional metals, alloys thereof, and mixtures thereof. The disclosed method can be run at lower temperatures than those used in the conventional steam reforming of alkanes.

U.S. Pat. No. 6,953,873 to Cortright et al., which is incorporated herein by reference, discloses a method of producing hydrocarbons from oxygenated hydrocarbon reactants, such as glycerol, glucose, or sorbitol. The method can take place in the vapor phase or in the condensed liquid phase (preferably in the condensed liquid phase). The method can include the steps of reacting water and a water-soluble oxygenated hydrocarbon having at least two carbon atoms, in the presence of a metal-containing catalyst. The catalyst can contain a metal selected from the group consisting of Group VIIIB transitional metals, alloys thereof, and mixtures thereof. These metals can be supported on supports that exhibit acidity or the reaction is conducted under liquid-phase conditions at acidic pHs. The disclosed method allows the production of hydrocarbon by the liquid-phase reaction of water with biomass-derived oxygenated compounds.

U.S. Pat. Nos. 6,964,757 and 6,964,758 to Cortright et al., which are incorporated herein by reference, disclose a method of producing hydrogen from oxygenated hydrocarbon reactants, such as methanol, glycerol, sugars (e.g. glucose and xylose), or sugar alcohols (e.g. sorbitol). The method can take place in the condensed liquid phase. The method can include the steps of reacting water and a water-soluble oxygenated hydrocarbon in the presence of a metal-containing catalyst. The catalyst contains a metal selected from the group consisting of Group VIIIB transitional metals, alloys thereof, and mixtures thereof. The disclosed method can be run at lower temperatures than those used in the conventional steam reforming of alkanes.

U.S. Pat. No. 4,223,001 to Novotny et al. discloses methods of generating hydrogen from an aqueous feedstock comprising a water-soluble alcohol, such as methanol or ethylene glycol, using a catalyst comprising a Group VIII metal, such as a homogeneous rhodium-containing catalyst (e.g., RhCl$_3$.3H$_2$O in the aqueous phase.

Cortright et al. describe the conversion of oxygenated compounds, methanol, ethylene glycol, glycerol, sorbitol, and glucose via aqueous phase reforming over a 3% Pt/Al$_2$O$_3$ catalyst. Reaction temperatures ranged from 498 to 538 K, system pressures ranged between 29 and 56 bar, and feed concentrations of 1 wt % oxygenated compound. Cortright, R. D.; Davda, R. R.; Dumesic J. A., Nature, Vol. 418, p. 964, 2002.

Davda et al. describe reaction kinetic studies of aqueous-phase reforming of 10 wt % ethylene glycol solutions over silica-supported metal catalysts. Reaction temperatures for this investigation were 483 and 498 K and reaction pressure of 22 bar. Results from this paper show that the overall catalytic activity of these catalyst decreases in the following order: Pt~Ni>Ru>Rh~Pd>Ir. Davda, R. R.; Shabaker J. W.; Huber, G. W.; Cortright, R. D.; Dumesic, J. A.; Appl. Cat. B: Environmental, Vol 43, p. 13, 2003.

Shabaker et al. describe reaction kinetic studies of aqueous-phase reforming of 10 wt % ethylene glycol solutions over Pt-black and Pt supported on TiO$_2$, Al$_2$O$_3$, activated carbon, SiO$_2$, SiO$_2$—Al$_2$O$_3$, ZrO$_2$, CeO$_2$, and ZnO. Reaction temperatures were 483 and 498 K, and the reaction pressures were 22.4 and 29.3 bar, respectively. High activity for the production of H$_2$ by aqueous-phase reforming was observed over Pt-black and over Pt supported on TiO$_2$, carbon, and Al$_2$O$_3$; moderate catalytic activity for the production of hydrogen is demonstrated by Pt supported on SiO$_2$—Al$_2$O$_3$ and ZrO$_2$; and lower catalytic activity is exhibited by Pt supported on CeO$_2$, ZnO, and SiO$_2$. Pt supported on Al$_2$O$_3$, and to a lesser extent ZrO$_2$, exhibits high selectivity for production of H$_2$ and CO$_2$ from aqueous-phase reforming of ethylene glycol. Shabaker, J. W.; Huber, G. W.; Davda, R. R.; Cortright, R. D.; Dumesic, J. A.; Catalysis Letters, Vol. 88, p. 1, 2003.

Davda et al. describe reaction conditions desired to generate hydrogen with low concentrations of CO via aqueous-phase reforming of ethylene glycol over a 3% Pt/Al$_2$O$_3$ catalyst. Reaction temperatures ranged from 498 K to 512 K, system pressure between 25.8 to 36.2 bar, and ethylene feed concentrations between 2 and 10 wt %. Davda, R. R; Dumesic J. A.; Angew. Chem. Int. Ed., Vol. 42, p. 4068, 2003.

Huber et al. describe the reaction of sorbitol to produce C1 through C6 alkanes over platinum-based catalyst with varying amounts of hydrogen added as a co-feed. In this paper, the platinum was loaded on either alumina or silica-alumina. This paper discussed the mechanism for this process through a bi-functional route involving acid-catalyzed dehydration reaction followed by a metal catalyzed hydrogenation reaction. Reaction temperatures were between 498 and 538 K, pressures between 25.8 to 60.7 bar, and feed concentrations of 5 wt % sorbitol. Huber, G. W.; Cortright, R. D.; Dumesic, J. A., Angew. Chem. Int. Ed., Vol. 43, p. 1549, 2004.

Davda et al. review aqueous-phase reforming of oxygenated compounds. Discussed are the effects of supports, supported metals, reaction conditions, and reactor configurations. Concentrations of oxygenated compounds were less than 10% in this paper. Davda, R. R.; Shabaker J. W.; Huber, G. W.; Cortright, R. D.; Dumesic, J. A.; Appl. Cat. B: Environmental, Vol 56, p. 171, 2005.

Huber et al. describe the effectiveness of tin modified nickel-based catalyst for the aqueous-phase reforming of oxygenated compounds such as ethylene glycol, glycerol, and sorbitol at 498 K and 538 K. Concentrations of oxygenated compounds studies in this investigation were less than 5 wt %. Huber, G. W.; Shabaker, J. W.; Dumesic, J. A.; Science, Vol. 300, p. 2075, 2003.

Previous patents and literature describe methods for the aqueous-phase reforming of water soluble oxygenated compounds at concentrations of 10 wt % or lower. Energy balances on the APR system indicate that significant energy losses can occur because of vaporization of water in the reactor system to maintain the partial pressure of water in the hydrogen gas bubbles formed in the reactor.

Thus, there exists a need for catalyst systems and processes that have higher activity levels to support high conversion of high concentrations of oxygenated hydrocarbon feedstocks in an aqueous reforming system.

SUMMARY

In a first embodiment, reforming catalysts are provided. The reforming catalysts preferably comprise a mixture of Group VIIB and Group VIII transition metals and mixtures thereof. Preferably, the reforming catalyst comprises Re and at least one transition metal selected from the group consisting of: Ir, Ni, Pd, Pt, Rh and Ru. Optionally, the catalyst further comprises Ce or La. Examples of suitable bimetallic catalysts include: IrRe, NiRe, PdRe, PtRe, $Rh_3Re$, RhRe, and RuRe. $Pt_{1.0}Re_{2.5}$ is an example of one particularly preferred catalyst.

The reforming catalyst can be adhered to an aqueous-stable support. For example, the catalyst can be adhered to a support comprising one or more materials selected from the group consisting of: carbon, zirconia, titania or ceria. Preferably, the catalyst is adhered to a carbon support. Carbon supports can be modified with other materials such as titanium, vanadium, tungsten or rhenium. In one particular aspect, the catalyst can be adhered to a support such that the combination of the catalyst and the support comprises 0.25%-10% by weight of the Group VIII metal on the catalyst, and the catalyst comprises Re and the Group VIII metal. The atomic ratio of Re to the Group VIII metal is preferably between 0.25 to 10. One preferred catalyst comprises $Pt_{1.0}Re_{2.5}$ adhered to a carbon support.

In a second embodiment, methods of reforming an oxygenated hydrocarbon from a feedstock solution of oxygenated hydrocarbon are provided that comprise the step of contacting the feedstock solution with a reforming catalyst. The oxygenated hydrocarbon is preferably a water-soluble hydrocarbon, including polyol compounds, with any suitable number of carbon atoms, such as water-soluble oxygenated hydrocarbons with 1 to 12 carbon atoms, preferably 1 to 6 carbons. Examples of preferred oxygenated hydrocarbons include ethylene glycol, glycerol, and sorbitol. Methods of reforming an oxygenated hydrocarbon include methods of producing hydrogen, as well as methods of producing mixtures of hydrogen and alkanes, from one or more oxygenated hydrocarbons in a feedstock. The feedstock solution can be an aqueous solution with at least 20 weight percent of the total feedstock solution of an oxygenated hydrocarbon having at least one oxygen. For example, the feedstock solution can comprise at least about 20%, 30%, 40%, or 50% of the oxygenated hydrocarbon.

The feedstock solution can be contacted with the reforming catalyst under conditions of reaction temperature and reaction pressure effective to produce hydrogen gas, as described herein. The reaction temperature and pressure are preferably selected to maintain the feedstock in the liquid phase. For example, the reaction temperature can be between about 80° C. and about 300° C. and the reaction pressure can be between about 10 bar (145 psi) and about 90 bar (1300 psi). More preferably, the reaction temperature can be between about 120° C. and about 300° C., even more preferably between about 150° C. and about 300° C., and the reaction pressure can be between about 10 bar (145 psi) and about 50 bar (725 psi). Liquid-phase modifiers such as water-soluable salts of alkali or alkali earth metals can optionally be added to the feedstock at a range of between 0.1 to 10 wt % of the aqueous-solution to optimize reaction products. For example, addition of compounds to increase the pH of the feedstock can increase the amount of hydrogen production in the reaction products.

The methods of reforming oxygenated hydrocarbons may produce a variety of useful reaction products, such as hydrogen, carbon dioxide and/or light hydrocarbons (e.g., methane, ethane, propane, butane, and pentane) from a feedstock comprising sorbitol or glycerol. In one aspect, methods of alkane production are provided that include contacting the feedstock solution with a reforming catalyst. The feedstock may include an aqueous solution having about 10-60% of one or more $C_1$-$C_6$ oxygenated hydrocarbon, preferably glycerol, ethylene glycol, and/or sorbitol. The feedstock may be contacted with a catalyst comprising one or more metals selected from the group consisting of platinum, rhodium and rhenium. In another aspect, methods of hydrogen production are provided that includes contacting the feedstock solution with a suitable reforming catalyst, as described herein.

In a third embodiment, methods of making a reforming catalyst are provided. In one aspect, a method of preparing a catalyst can include the step of oxidizing a carbon support by heating the carbon support to a temperature of about 450° C., introducing air to form an activated carbon support, and contacting the carbon support with a catalyst. For example, activated carbon can be heated to a desired temperature in a stream of inert gas, such as nitrogen, and then contacted with a stream of air at a suitable flow rate, added to the nitrogen. The carbon can be treated for a suitable period and then allowed to cool under flowing nitrogen. The method of preparing a catalyst further comprises the step of incorporating a metal oxide in the activated carbon support by incipient wetting of the activated carbon support with a solution comprising a metal alkoxide comprising the metal oxide. Preferably, the metal oxide is incorporated without suspending the carbon support in solvent. For example, functionalized carbon surfaces can be modified by impregnation of metal oxides prior to impregnation of catalyst precursors. Organic solutions of suitable metal oxides, such as titanium n-butoxide or vanadium oxide triisopropoxide in anhydrous isopropanol, can be added by incipient wetting to air oxidation functionalized carbon, and the wetted carbon can be subsequently dried.

DETAILED DESCRIPTION

Figure 1:
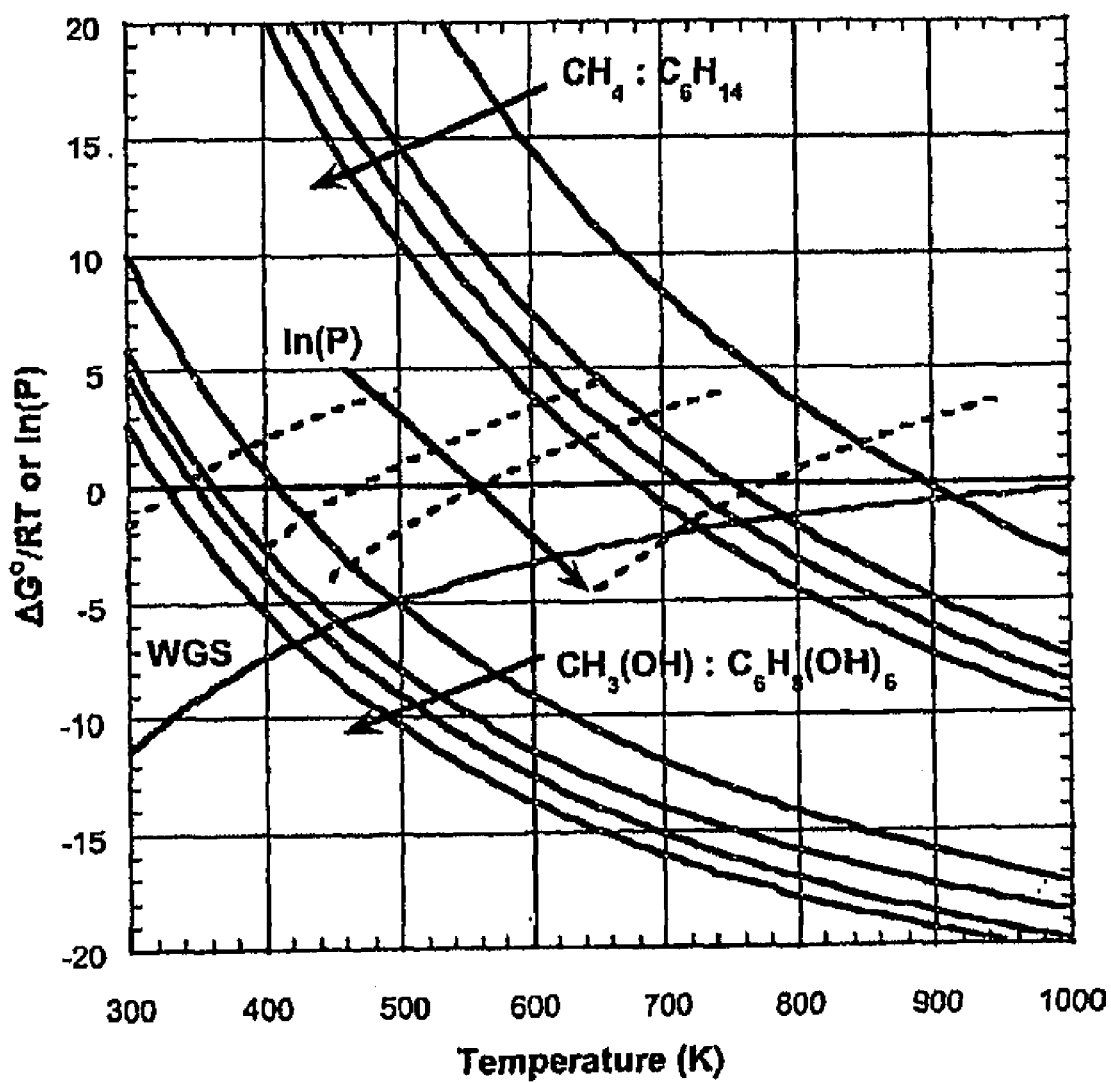
FIG. 1 is a graph depicting the thermodynamics for the conversion of hydrocarbons and oxygenated hydrocarbons to carbon monoxide and hydrogen ($H_2$)
Figure 2:
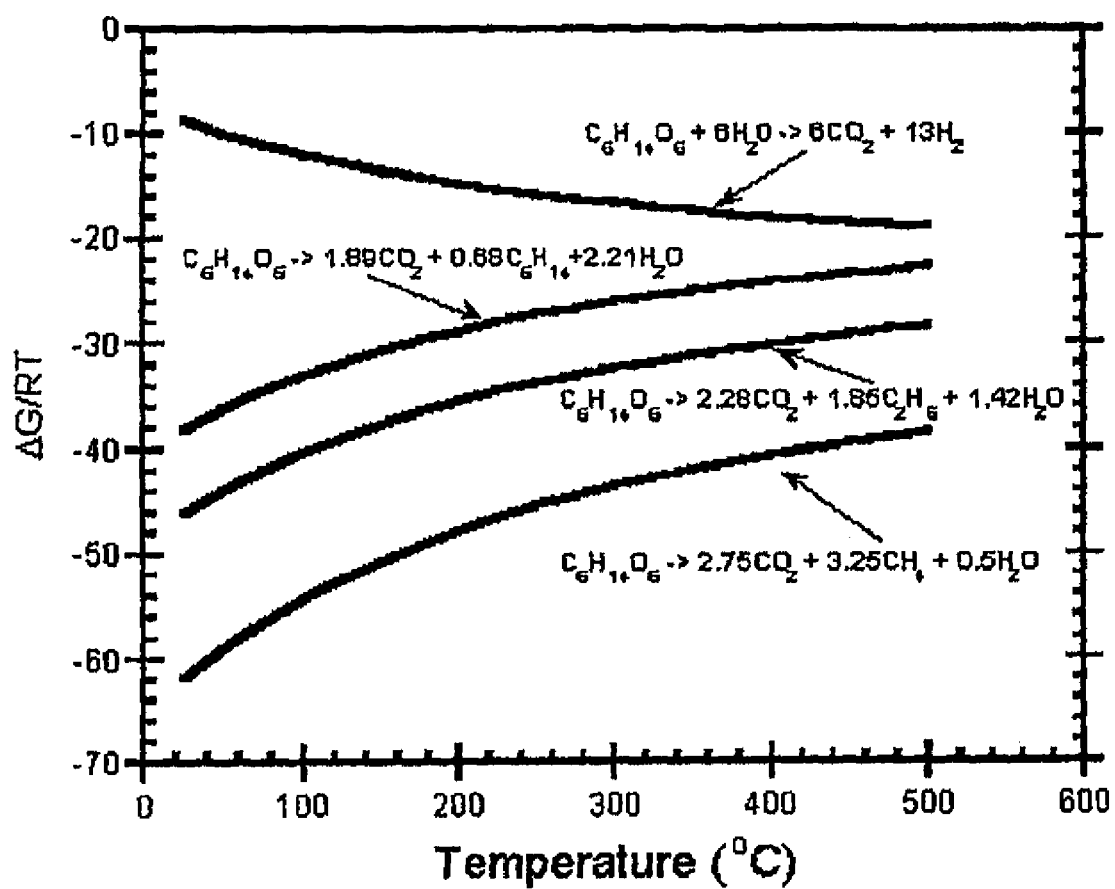
FIG. 2 is a graph depicting the thermodynamics for the conversion of sorbitol to hydrogen, carbon dioxide, water and various hydrocarbons.

Various methods are described herein for reforming high concentrations of oxygenated hydrocarbons with water at low temperatures and in the liquid-phase. Unless otherwise indicated, the following terms shall be defined herein as indicated below.

The term "reforming" shall generically denote the overall reaction of an oxygenated hydrocarbon and water to yield a product mixture comprising hydrocarbons and/or hydrogen and $CO_2$, regardless of whether the reaction takes place in the gaseous phase or in the condensed liquid phase. Where the distinction is important, it shall be so noted.

The term "Group VIII" transition metal refers to an element selected from the group consisting of: Fe, Co, Ni, Ru, Rh, Pd, Os, Ir, Pt, Hs, Mt and Ds, in any oxidation state.

The term "Group VIIB" transition metal refers to an element selected from the group consisting of: Mn, Tc, Re and Bh, in any oxidation state.

When the reforming of oxygenated hydrocarbons is carried out in the liquid phase, the present invention makes it possible to produce hydrocarbons from aqueous solutions of oxygenated hydrocarbons having limited volatility, such as sugars (glucose and xylose) and heavier molecular weight polyols such as xylitol and sorbitol.

Abbreviations and Definitions:

"GC"=gas chromatograph or gas chromatography.

"GHSV"=gas hourly space velocity.

"psig"=pounds per square inch relative to atmospheric pressure (i.e., gauge pressure).

"Space Velocity"=the mass/volume of reactant per unit of catalyst per unit of time.

"TOF"=turnover frequency.

"WHSV"=weight hourly space velocity=mass of oxygenated compound per mass of catalyst per h.

"WGS"=water-gas shift.

Oxygenated Hydrocarbons

Oxygenated hydrocarbons for the reforming processes described herein are preferably water-soluble. Desirably, the oxygenated hydrocarbon has from 1 to 12 carbon atoms, and more preferably from 1 to 6 carbon atoms. For feedstock concentrations of about 30% oxygenated hydrocarbons with 1 to 6 carbon atoms are particularly preferred. Preferred oxygenated hydrocarbons comprise at least 1 oxygen atom in the oxygenated hydrocarbon, and oxygen-to-carbon ratios ranging from 0.50:1.00 to 1.50:1.00, including ratios of 0.25:1.00, 0.33:1.00, 0.66:1.00, 0.75:1.00, 1.00:1.00, 1.25:1.00, 1.5:1.00, as well as ratios therebetween. Preferably oxygenated hydrocarbons have an oxygen-to-carbon ratio of 1:1. The oxygenated hydrocarbon can also be a polyol. Nonlimiting examples of preferred water-soluble oxygenated hydrocarbons can be selected from the group consisting of: methanol, ethanol, ethanediol, ethanedione, acetic acid, propanol, propanediol, propionic acid, glycerol, glyceraldehyde, dihydroxyacetone, lactic acid, pyruvic acid, malonic acid, butanediols, butanoic acid, aldotetroses, tautaric acid, aldopentoses, aldohexoses, ketotetroses, ketopentoses, ketohexoses, and alditols. From among the 6-carbon oxygenated hydrocarbons, aldohexoses and corresponding alditols are particularly preferred, with glucose and sorbitol being the most preferred. Xylose, arabinose, arabinol and xylitol are particularly preferred oxygenated compounds having 5 carbon atoms. Sucrose is a preferred oxygenated hydrocarbon having more than 6 carbon atoms.

Vapor-phase reforming requires that the oxygenated hydrocarbon reactants have a sufficiently high vapor pressure at the reaction temperature so that the reactants are in the vapor phase. In particular, the oxygenated hydrocarbon compounds preferred for use in the vapor phase method of the present invention include, but are not limited to, methanol, ethanol, ethanediol, glycerol, and glyceraldehyde. When the reaction is to take place in the liquid phase, sugars such as sucrose, glucose, xylose and polyols such as xylitol and sorbitol are the most preferred oxygenated hydrocarbons.

In the methods of the present invention, the oxygenated hydrocarbon compound is preferably combined with water to create an aqueous solution. The water-to-carbon ratio in the solution is preferably from about 0.5:1 to about 7:1, including ratios therebetween such as 1:1, 2:1, 3:1, 4:1, 5:1, 6:1 and any ratios between these values. This range is provided as one example of a non-limiting, preferred range. Water-to-carbon ratios outside this range are also included within the scope of this invention. The feedstock solution can be an aqueous solution with at least 20 weight percent of the total feedstock solution of an oxygenated hydrocarbon having at least one oxygen. For example, the feedstock solution can comprise at least about 20%, 30%, 40%, 50% or 60% of one or more oxygenated hydrocarbons. Unless otherwise specified, references to a percentage of oxygenated hydrocarbon in the feedstock refers to the total amount oxygenated hydrocarbon species in the feed stock solution, which can include mixtures of multiple oxygenated hydrocarbon species.

Preferably the balance of the feedstock solution is water. In some embodiments, the feedstock solution consists essentially of water, one or more oxygenated hydrocarbons, and, optionally, one or more of the feedstock modifiers described herein, such as alkali or alkali earth salts or acids. The feedstock solution can preferably contain negligible amounts of hydrogen, preferably less than about 1 bar partial pressure. In preferred embodiments, hydrogen is not added to the feedstock.

Figure 3:
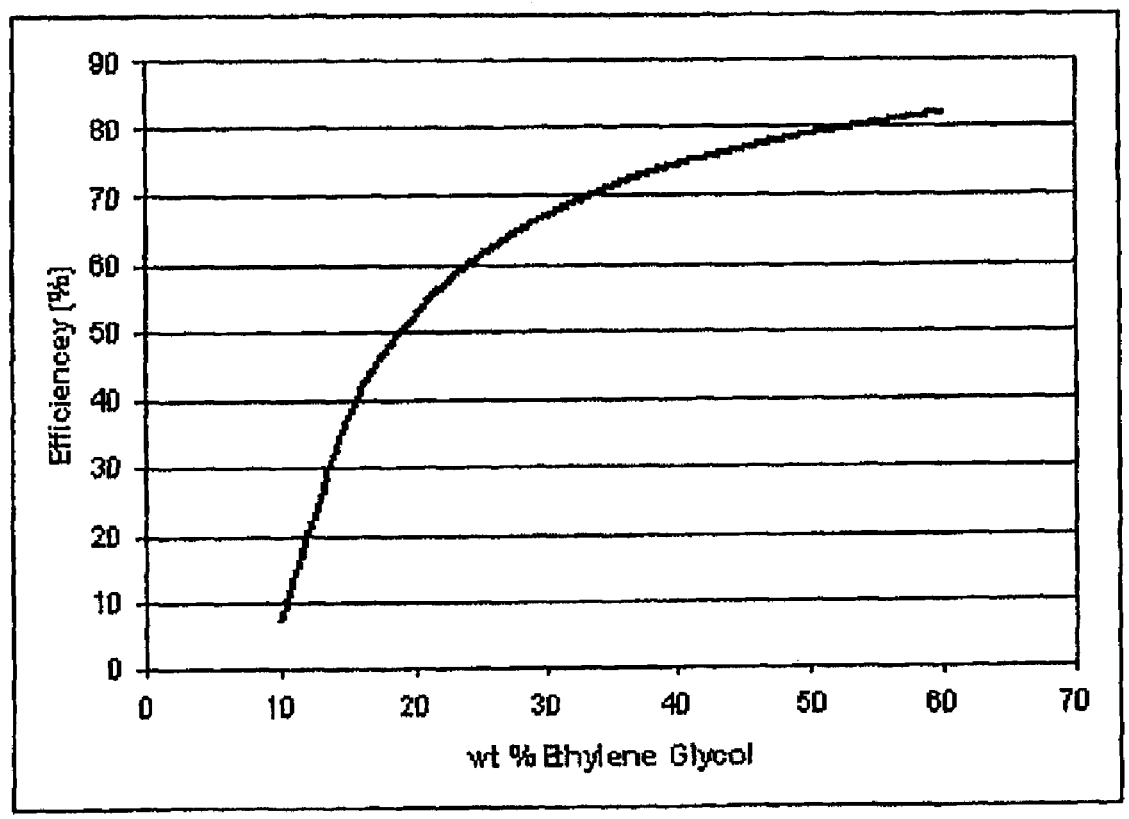
FIG. 3 is a graph depicting the effect of feed composition on thermal efficiency at 100% conversion in an aqueous phase reforming system.

An aqueous reforming process can be operated at feed concentrations in this range using different catalysts. For example, Shabaker et al. describe the aqueous-phase reforming of 5 and 63 wt % solutions of ethylene glycol of a NiSn catalyst. Shabaker, J. W.; Simonetti, D. A.; Cortright, R. D.; Dumesic, J. A.; J. Catal., Vol. 231, p. 67, 2005. As FIG. 3 shows, the thermal efficiency of the system can be improved by operating the system with higher concentrations of feedstock. FIG. 3 shows that as the feed concentration is increased from 10 wt % to 60 wt %, the calculated efficiency of the system increases from less that 10% to greater than 80% at a 100% conversion of the ethylene glycol. FIG. 3 was constructed using thermodynamic and vapor pressure data taken from Chemical Properties Handbook, C. L. Yaws, McGraw Hill, 1999.

Catalysts

The metallic catalyst systems preferred for use in the present invention comprise of one or more Group VIII metal combined with one or more of a Group VIIB metal. The preferred Group VIIB metals would be rhenium or manganese. The preferred Group VIII metals would be platinum, rhodium, ruthenium, palladium, nickel or combination thereof. Preferred loadings of the Group VIII metals would be in the range of 0.25 wt % to 25 wt % on the carbon including weight percentages of 0.10% and 0.05% increments between these values, such as 1.00%, 5.00%, 10.00%, 12.50%, 15.00% and 20.00%. The preferred atomic ratio of the Group VIIB to the Group VIII metal is in the range of 0.25-to-1 to 10-to-1, including ratios therebetween such as 0.50, 1.00, 2.50, 5.00, and 7.50-to-1.

The preferred catalyst composition is further achieved by the addition of oxides of Group IIIB and the associated rare earth oxides. In this case the preferred components would be oxides of either lanthanium or cerium. The preferred atomic ratio of the Group IIIB compounds to the Group VIII metal is in the range of 0.25-to-1 to 10-to-1, including ratios therebetween such as 0.50, 1.00, 2.50, 5.00, and 7.50-to-1.

Unless otherwise specified, the recitation of a catalyst composition as "X:Y" herein, where X and Y are metals, refers to a group of catalyst compositions comprising at least metals X and Y in any suitable stoichiometric combination, and optionally including other materials. Similarly, the recitation of a catalyst composition as "$X_{1.0}Y_{1.0}$" refers herein to a composition comprising at least metals X and Y in a 1:1 stoichiometric molar ratio. Accordingly, particularly preferred catalytic compositions are bimetallic metal compositions described by the formula X:Y, where X is a Group VIII metal and Y is a Group VIIB metal. For example, the catalysts designated "Re:Pt" include the bimetallic catalysts $Re_{1.0}Pt_{1.0}$ and $Re_{2.5}Pt_{1.0}$. Furthermore, recitation of a bimetallic catalyst X:Y can include additional materials besides X and Y, such as La or Ce. For example, the catalysts designated "Re:Rh" herein include catalysts such as $Re_{1.0}Rh_{1.0}$, $Re_{1.0}Rh_{3.8}$, $Re_{1.0}Rh_{2.0}Ce_{2.0}$, $Re_{1.0}Rh_{1.0}Ce_{1.0}$, and $Re_{1.0}Rh_{1.0}La_{3.0}$.

In some embodiments, the catalysts can be provided with a suitable support. Catalyst systems can be supported on a form of support that is stable at the chosen reaction conditions. Any suitable support can be used, but supports are preferably sufficiently stable in a feedstock solution, such as an aqueous feedstock solution, to function at a desired level. One particularly preferred catalyst support is carbon. It is preferred that such carbon supports have relatively high surface areas (greater than 100 square meters per gram). Such carbons include activated carbon (granulated, powdered, or pelletized), activated carbon cloth, felts, or fibers, carbon nanotubes or nanohorns, carbon fullerene, high surface area carbon honeycombs, carbon foams (reticulated carbon foams), and carbon blocks. The carbon may be produced via either chemical or steam activation of peat, wood, lignite, coal, coconut shells, olive pits, and oil based carbon. One preferred support is granulated activated carbon produced from coconuts. Other useful catalyst supports for the practice of the invention include, but are not limited to: silica, silica-alumina, and alumina. Preferably, the catalyst system is platinum on silica or silica-alumina, with the platinum being further alloyed or admixed with nickel or ruthenium. The support may also be treated, as by surface-modification, to modify surface moieties such hydrogen and hydroxyl. Surface hydrogen and hydroxyl groups can cause local pH variations that would affect catalytic efficiency. The support can be modified, for example, by treating it with a modifier selected from the group consisting sulfates, phosphates, tungstenates, and silanes.

It is preferred that the chosen carbon may be pretreated with either steam, oxygen (from air), inorganic acids, or hydrogen peroxide to provide more surface oxygen sites. The preferred pretreatment would be to use either oxygen (from air) or hydrogen peroxide.

The pretreated carbon can be modified by the addition of oxides of Group IVB and Group VB. It is preferred to use oxides of titanium, vanadium, zirconia and mixtures thereof.

The catalyst systems of the present invention can be prepared by conventional methods known to those in the art. These methods include evaporative impregnation techniques, incipient wetting techniques, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity and the like.

Reforming Methods

The liquid phase reforming method of the present invention should generally be carried out at a temperature at which the thermodynamics of the proposed reaction are favorable. The pressure selected for the reactions varies with the temperature. For condensed phase liquid reactions, the pressure within the reactor must be sufficient to maintain the reactants in the condensed liquid phase at the reactor inlet.

The vapor phase reforming method of the present invention should be carried out at a temperature where the vapor pressure of the oxygenated hydrocarbon compound is at least about 0.1 atm (and preferably a good deal higher), and the thermodynamics of the reaction are favorable. This temperature will vary depending upon the specific oxygenated hydrocarbon compound used, but is generally in the range of from about 100° C. to about 450° C. for reactions taking place in the vapor phase, and more preferably from about 100° C. to about 300° C. for vapor phase reactions. For reactions taking place in the condensed liquid phase, the preferred reaction temperature should not exceed about 300° C.

The condensed liquid phase method of the present invention may also optionally be performed using a modifier that increases the activity and/or stability of the catalyst system. It is preferred that the water and the oxygenated hydrocarbon are reacted at a suitable pH of from about 1.0 to about 10.0, including pH values in increments of 0.1 and 0.05 therebetween. Generally, the modifier is added to the feedstock solution in an amount ranging from about 0.1% to about 10% by weight as compared to the total weight of the catalyst system used, although amounts outside this range are included within the present invention.

Optionally, alkali or alkali earth salts can be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4 to about pH 10 can improve hydrogen selectivity of reforming reactions.

Methods of alkane production are provided that include contacting the feedstock solution with a reforming catalyst. The feedstock may include an aqueous solution having about 10-60%, preferably 20% or 30% or more, of one or more $C_1$-$C_6$ oxygenated hydrocarbon, preferably glycerol, ethylene glycol, and/or sorbitol. The feedstock may be contacted with a catalyst comprising one or more metals selected from the group consisting of platinum, rhodium and rhenium. As described in the examples, suitable catalysts for use in methods of producing alkanes include PtRe and RhRe catalysts with varying amounts of each metal. Preferred methods for alkane production provide products containing about 3-50%, 5-25% or 10-20% alkanes in the product stream. Preferably, the alkanes produced have 1, 2, 3, 4, 5, 6, 7, 8 or more carbons, and may be straight or branched hydrocarbons.

Optionally, acidic compounds may be added to a feedstock or reactor system to provide increased alkane selectivity of the reforming reactions. It is preferred that the water-soluble acid is selected from the group consisting of nitrate, phosphate, sulfate, and chloride salts, and mixtures thereof. If an optional acidic modifier is used, it is preferred that it be present in an amount sufficient to lower the pH of the aqueous feed stream to a value between about pH 1 and about pH 4. Lowering the pH of a feed stream in this manner can increase the proportion of alkanes in the reaction products.

Described below are methods to generate both hydrogen and alkanes via aqueous-phase reforming of oxygenated hydrocarbons that contain at least one carbon and one oxygen. These methods utilize a combination of Group VIIB and Group VIII metals supported on activated carbon generated from coconut, the carbon may be functionalized either by an acid treatment, treatment with hydrogen peroxide, or treatment with oxygen, the carbon support can further be functionalized by the addition oxides of either titanium, vanadium, tungsten, molybendum. The performance is further enhanced by the addition of oxides of Group IIIB and the associated rare earth. The process is thermally efficient if the process is run at feed concentration of greater than 20 wt % oxygenated compound, preferably greater than 30 wt %, more preferably greater than 40 wt % or 50 wt %.

In one aspect, preferred compositions of matter are provided. The compositions may be isolated before, during or after performing one or more methods or processes described herein, and may be isolated within a portion of a reactor system. One preferred composition comprises in one or more phases: an APR catalyst composition, sorbitol, hydrogen, carbon dioxide, and hydrocarbons such as methane, ethane, propane, butane, pentane, and hexane. Another preferred composition comprises, in one or more phases: an APR catalyst composition, glycerol, hydrogen, carbon dioxide and light hydrocarbons such as methane, ethane, propane, butane and pentane. The catalyst composition in both compositions preferably include one or more metals selected from the group consisting of: platinum, rhenium and rhodium. In particular, a composition comprises a solid phase including a catalyst comprising platinum, rhenium and/or rhodium, an aqueous phase including sorbitol, a gas phase including hydrogen, carbon dioxide, and methane, and organic or gas phases including ethane, propane, butane, pentane and hexane. Another composition comprises a solid phase including a catalyst comprising platinum, rhenium and/or rhodium, an aqueous phase including glycerol, a gas phase including hydrogen, carbon dioxide, and methane, and organic or gas phases including ethane, and propane.

EXAMPLES

The following examples are to be considered illustrative of various aspects of the invention and should not be construed to limit the scope of the invention, which are defined by the appended claims.

Example 1

Method 1

Monometallic catalyst systems supported on activated carbons were prepared by impregnating the carbon with solutions of metal precursors using incipient wetness techniques. (1) Activated carbons to be impregnated were dried under vacuum at ~100° C. overnight and stored in sealed containers until used. (2) A solution containing the metal precursor(s), volume equal to incipient wetness volume for the carbon to be impregnated, was applied drop wise, while stirring, to the activated carbon. (3) The wetted carbon was dried under vacuum as in step 1. (4) If additional applications were required to achieve the desired metal loading, steps 2 and 3 were repeated until sufficient metal precursor had been applied.

Example 2

5% wt. Pt on C

A 5 wt % platinum catalyst supported on activated carbon was prepared according to the general method of Example 1. An aqueous solution, 22.49 g, containing 3.34 g of dihydrogen hexachloroplatinate (IV) hexahydrate was added to 22.49 g activated carbon (Calgon OLC-AW, sieved to 18-40 mesh). The mixture was dried at 100° C. under vacuum.

Example 3

5% Ru on C

A 5 wt % ruthenium catalyst supported on activated carbon was prepared according to the general method of Example 1. An aqueous solution, 38 mL, containing 0.98 g of ruthenium (III) nitrosylnitrate (Alfa Aesar, 1.5% Ru) was added to 47.52 g activated carbon (Calgon OLC-AW, sieved to 18-40 mesh). The mixture was dried at 100° C. under vacuum. Three additional applications using 38 mL of this solution, then a last application, using 14 mL of this solution diluted to 38 mL, were performed. The carbon mixture was dried at 100° C. under vacuum between each application.

Example 4

5% wt. Rh on C

A 5 wt % rhodium catalyst supported on activated carbon was prepared according to the general method of Example 1. An aqueous solution, 38 mL, containing 18.54 g of rhodium nitrate solution(Alfa Aesar, 13.84% Rh) was added to 47.51 g activated carbon (Calgon OLC-AW, sieved to 18-40 mesh). The mixture was dried at 100° C. under vacuum.

Example 5

5% wt. Re on C

A 5 wt % rhenium catalyst supported on activated carbon was prepared according to the general method of Example 1. An aqueous solution, 7.6 mL, containing 0.882 g of perrhenic acid solution (Alfa Aesar, 76.41% HReO4) was added to 9.502 g activated carbon (Calgon OLC-AW, sieved to 18-40 mesh). The mixture was dried at 100° C. under vacuum.

Example 6

5% wt. Pd on C

A 5 wt % palladium catalyst supported on activated carbon was prepared according to the general method of Example 1. An aqueous solution, 7.6 mL, containing 5.916 g of palladium (II) nitrate (Alfa Aesar, 8.5% Pd) was added to 9.501 g activated carbon (Calgon OLC-AW, sieved to 18-40 mesh). The mixture was dried at 100° C. under vacuum.

Example 7

5% wt. Ir on C

A 5 wt % iridium catalyst supported on activated carbon was prepared according to the general method of Example 1. An aqueous solution, 62 mL, containing 5.03 g of dihydrogen hexachloroiridate (IV) hydrate (Strem, 47.64% Ir) was added to 44.87 g activated carbon (Calgon OLC-AW, sieved to 18-40 mesh). The mixture was dried at 100° C. under vacuum.

Example 8

15% wt. Ni on C

A 15 wt % nickel catalyst supported on activated carbon was prepared according to the general method of Example 1. An aqueous solution, 7.3 mL, containing 7.807 g of nickel (II) nitrate hexahydrate (Alfa Aesar, 19.4% Ni) was added to 8.587 g activated carbon (Calgon OLC-AW, sieved to 12-40 mesh). The mixture was dried at 100° C. under vacuum.

Example 9

Figure 4:
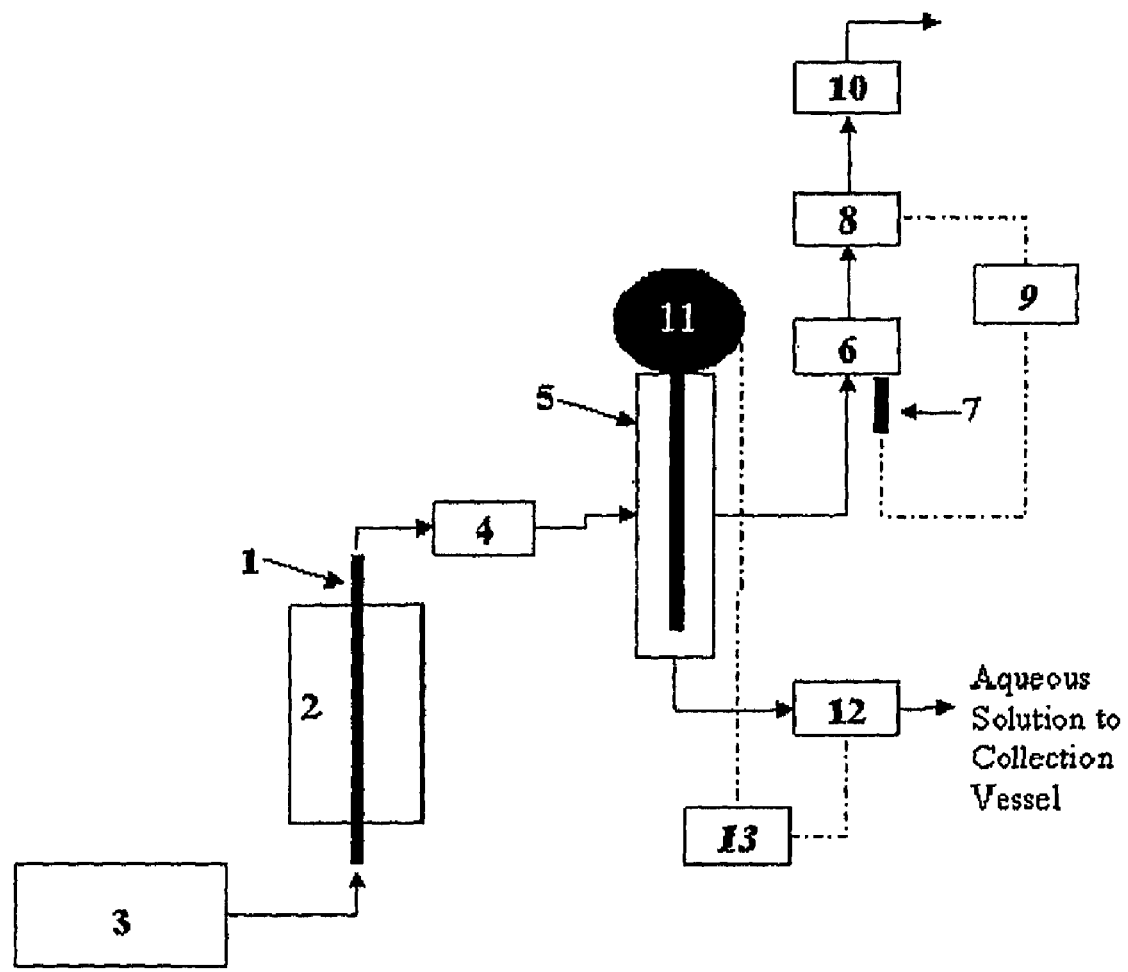
FIG. 4 is a schematic diagram of a reactor system that can be used to evaluate the aqueous phase reforming activity of catalysts according to an embodiment of the present invention.

Catalysts were evaluated for APR activity using test systems illustrated in FIG. 4.

Catalysts are loaded into a stainless steel tube reactor 1 which is installed in an aluminum block heater 2 to maintain isothermal conditions. The reaction temperature is controlled by the temperature control subsystem. The critical components of the temperature control subsystem (not shown in FIG. 4) are a thermocouple inserted into the tube reactor, resistive heaters mounted on the aluminum block, and a PID controller.

Substrate solutions (i.e., feedstock solutions) are continuously fed into the reactor using an HPLC pump 3. The material exiting the reactor is cooled as it passes through heat exchanger 4 before entering the phase separator 5.

Gasses exit the phase separator via the gas manifold 6 which is maintained at constant pressure by the pressure control subsystem. The critical components of the pressure control subsystem are the pressure sensor 7 pressure control valve 8 and PID controller 9. The quantity of gas released by the pressure control valve 8 is measured by mass flow meter 10. The composition of this gas is monitored by gas chromatography.

The liquid level in phase separator 5 is maintained at constant level by the level control subsystem. The components of the level control subsystem include the level sensor 11 in the phase separator, a level control valve 12 and PID controller 13. The aqueous solution drained from the phase separator during a catalyst evaluation experiment is collected and the quantity collected measured gravimetrically. Analysis of this solution may include, pH, total organic carbon concentration, GC to determine the concentrations of unreacted substrate and specific intermediates and side products.

Example 10

Monometallic catalyst systems described in Examples 1 thru 8 were tested in the apparatus described in Example 9. The catalysts were treated under flowing hydrogen at 250° C., before the liquid feed containing 10 wt % ethylene glycol was introduced to the catalyst at 230° C. Table 1 below describes the results of reforming the ethylene glycol solution over the catalyst at 430 psig. Table 1 shows that of the Group VIII carbon-supported monometallic catalytic materials, that platinum and ruthenium show appreciable activity. Carbon-supported rhenium also shows some reforming activity.

TABLE 1

Activity of Monometallic Catalysts for APR of 10% Ethylene Glycol

| Catalyst | Example | APR T(° C.) | P (PSIG) | WHSV $(hr^{-1})^a$ | Conversion to Gas (%) | Gas Composition | | |
|---|---|---|---|---|---|---|---|---|
| | | | | | | $H_2$ (%) | Alkanes (%) | $CO_2$ (%) |
| 5% Pt | 2 | 230 | 430 | 0.80 | 13% | 84% | 1% | 15% |
| 5% Ru | 3 | 230 | 430 | 0.77 | 27% | 9% | 39% | 52% |
| 5% Rh | 4 | 230 | 430 | 0.71 | 0% | NA | NA | NA |
| 5% Re | 5 | 230 | 430 | 0.84 | 4% | 67% | 4% | 29% |
| 5% Pd | 6 | 230 | 430 | 0.78 | 0% | NA | NA | NA |
| 5% Ir | 7 | 230 | 430 | 2.38 | 0% | NA | NA | NA |
| 15% Ni | 8 | 230 | 430 | 0.58 | 0% | NA | NA | NA |

$^a$Weight hour space velocities (WHSV) are based on feed rate of oxygenated substrate

Example 11

ReIr Bimetallic Catalyst, 5% wt. Ir, 1 Molar Ratio Re:Ir

Perrhenic acid solution (Alfa Aesar, 76.41% HReO$_4$), 0.87 g was diluted to 7.6 mL with DI water and added by incipient wetting to 10.00 g of 5 wt % Ir on Carbon catalyst from Example 7. The mixture was dried at 100° C. under vacuum.

Example 12

ReNi Bimetallic Catalyst, 5% wt. Ni, 1:16 Molar Ratio Re:Ni

Nickel (II) nitrate hexahydrate (Alfa Aesar, 19.4% Ni), 2.577 g, and Perrhenic acid solution (Alfa Aesar, 76.4% HReO$_4$), 0.163 g were dissolved in enough DI water to make a 7.6 mL solution. This solution was added by incipient wetting to 9.409 g activated carbon (Calgon OLC-AW, sieved to 18-40 mesh). The mixture was dried at 100° C. under vacuum.

Example 13

RePd Bimetallic Catalyst, 5% wt. Pd, 1:1 Molar Ratio Re:Pd

An aqueous solution, 7.6 mL, containing 4.577 g Perrhenic acid solution (Alfa Aesar, 76.4% HReO$_4$) and 5.906 g Palladium (II) nitrate (Alfa Aesar, 8.5% Pd) was added to 9.503 g activated carbon (Calgon OLC-AW, sieved to 18-40 mesh) by incipient wetting. The mixture was dried at 100° C. under vacuum.

Example 14

RePt Bimetallic Catalyst, 5% wt. Pt, 1:1 Molar Ratio Re:Pt)

A 5 wt % platinum catalyst supported on activated carbon was prepared according to the general method of Example 1. An aqueous solution, approximately 26 mL, containing 4.261 g of dihydrogen hexachloroplatinate (IV) hexahydrate (Alfa Aesar, 39.85% Pt) was added to 32.34 g activated carbon (Calgon OLC-AW, sieved to 18-40 mesh). The mixture was dried at 100° C. under vacuum. An additional application of aqueous solution, 7.6 mL, containing 0.87 g of perrhenic acid solution (Alfa Aesar, 76.41% $HReO_4$) was added to 10.03 g of the dried platinum/carbon mixture. The mixture was dried at 100° C. under vacuum.

Example 15

ReRh Bimetallic Catalyst, 5% wt. Rh, 1:3.8 Molar Ratio Re:Rh

An aqueous solution, approximately 7.6 mL, containing 3.55 g of rhodium (III) nitrate (Alfa Aesar, 13.93% Rh) was added to 9.51 g activated carbon (Calgon OLC-AW, sieved to 18-40 mesh) by incipient wetting. The mixture was dried at 100° C. under vacuum. An additional application of aqueous solution, 7.6 mL, containing 0.42 g of perrhenic acid solution (Alfa Aesar 76.41% $HReO_4$) was performed. The mixture was dried at 100° C. under vacuum.

Example 16

ReRh Bimetallic Catalyst, 5% wt. Rh, 1:1 Molar Ratio Re:Rh

An aqueous solution, 24.2 mL, containing 1.60 g perrhenic acid solution (Alfa Aesar, 76.41% $HReO_4$) was added to 10.01 g dry Degussa catalyst G106 NB/W 5 wt % Rh by incipient wetting. The mixture was dried at 100° C. under vacuum.

Example 17

ReRu Bimetallic Catalyst, 5% wt. Ru, 1:1 Molar Ratio Re:Ru)

Perrhenic acid solution (Alfa Aesar, 76.41% $HReO_4$), 1.63 g was diluted to 7.3 mL with DI water and added by incipient wetting to 10.01 g of 5 wt % Ru on Carbon catalyst from Example 3. The mixture was dried at 100° C. under vacuum.

Example 18

The rhenium modified catalyst systems described in Examples 11 thru 17 were tested in the apparatus described in Example 9. The catalysts were treated under flowing hydrogen at 250° C., before the liquid feed containing 10 wt % ethylene glycol was introduced to the catalyst at 230° C. Table 2 below describes the results of reforming the ethylene glycol solution over the catalyst at 430 psig. Table 2 shows that the combination of rhenium and Group VIII metals supported on activated carbon significantly enhances the activity for the reforming of ethylene glycol compared to the results of Example 10.

TABLE 2

Activity of Monometallic Catalysts for APR of 10% Ethylene Glycol

| Catalyst (MRe) | Example | Wt % M | Molar Ratios (Re:M) | WHSV $(hr^{-1})^a$ | Conversion to Gas (%) | Gas Composition | | |
|---|---|---|---|---|---|---|---|---|
| | | | | | | $H_2$ (%) | Alkanes (%) | $CO_2$ (%) |
| IrRe | 11 | 5% Ir | 1:1 | 0.76 | 76% | 39% | 19% | 35% |
| NiRe | 12 | 5% Ni | 1:16 | 0.68 | 4% | 74% | 20% | 6% |
| PdRe | 13 | 5% Pd | 1:1 | 0.73 | 20% | 54% | 27% | 19% |
| PtRe | 14 | 5% Pt | 1:1 | 0.72 | 74% | 38% | 36% | 28% |
| RhRe | 15 | 5% Rh | 1:3.8 | 0.80 | 75% | 65% | 6% | 28% |
| RhRe | 16 | 5% Rh | 1:1 | 1.73 | 100% | 52% | 20% | 28% |
| RuRe | 17 | 5% Ru | 1:1 | 1.98 | 83% | 21% | 45% | 32% |

$^a$Weight hour space velocities (WHSV) are based on feed rate of oxygenated substrate.

Example 19

RhReCe Catalyst, 5% wt. Rh, 1:2:2 Molar Ratio Re:Rh:Ce

An aqueous solution, 7.6 mL, containing 3.64 g of rhodium (III) nitrate (Alfa Aesar, 13.93% Rh), 0.82 g of perrhenic acid solution (Alfa Aesar, 76.49% $HReO_4$), 2.18 Cerium (III) nitrate was added to 9.50 g activated carbon (Calgon OLC-AW, sieved to 18-40 mesh) by incipient wetting. The mixture was dried at 100° C. under vacuum.

Example 20

Hydrogen peroxide has been used to functionalize activated carbons to provide improved supports for APR catalysts. S. R. de Miguel, O. A. Scelza, M. C. Roman-Martinez, C. Salinas Martinez de-Lecea, D. Cazorla-Amoros, A. Linares-Solano, Applied Catalysis A: General 170 (1998) 93. Activated carbon, 45 g, was added slowly to 1200 ml of 30% hydrogen peroxide solution. After addition of the carbon was completed, the mixture was left overnight. The aqueous phase was decanted and the carbon was washed three times with 1200 mL of DI water, then dried under vacuum at 100° C.

Example 21

RhReCe Catalyst, 5% wt. Rh, 1:1:1 Molar Ratio Re:Rh:Ce

Hydrogen peroxide functionalized carbon was prepared using the method described in Example 20 and Calgon OLC-AW, sieved to 18-40 mesh. After functionalization, the carbon was dried at 100° C. under vacuum. An aqueous solution, 7.6 mL, containing 2.12 g Cerium (III) nitrate was added by incipient wetting to 9.46 g of the hydrogen peroxide functionalized carbon. The mixture was dried at 100° C. under vacuum. An additional application of aqueous solution, 7.6 mL, containing 3.64 g rhodium (III) nitrate (Alfa Aesar, 12% Rh) and 1.61 g perrhenic acid solution was performed. The mixture was dried at 100° C. under vacuum.

Example 22

RhReLa Catalyst, 5% wt. Rh, 1:1:3 Molar Ratio Re:Rh:La

A 5 wt % rhodium catalyst supported on activated carbon was prepared according to the general method of Example 1. An aqueous solution, approximately 7.6 mL, containing 3.72 of rhodium (III) nitrate (Alfa Aesar, 13.65 wt % Rh) was added to 9.5 g activated carbon (Calgon OLC-AW, sieved to 18-40 mesh). The mixture was dried at 100° C. under vacuum. An additional application of aqueous solution, 7.6 mL, containing 1.60 g perrhemic acid solution (Alfa Aesar, 76.41% $HReO_4$) and 6.33 g Lanthanum (III) nitrate hexahydrate (Alfa Aesar, 99.9% $La(NO_3)_3$) was performed. The mixture was dried at 100° C. under vacuum.

Example 23

The Rh/Re catalysts modified with Group IIIB compounds described in Examples 19 thru 22 were tested in the apparatus described in Example 9. The catalysts were treated under flowing hydrogen at 250° C., before the liquid feed containing 10 wt % ethylene glycol was introduced to the catalyst at 230° C. Table 3 below describes the results of reforming the ethylene glycol solution over the catalyst at 430 psig. Table 3 shows the addition of these Group IIIB compounds enhances the selectivity to hydrogen.

TABLE 3

Activity of RhRe Catalysts attenuated with Ce or La for APR of 10% Ethylene Glycol

| | | | Molar Ratios | | | Gas Composition | | |
|---|---|---|---|---|---|---|---|---|
| Catalyst | Example | Wt % Rh | (Re:Rh:Ce or La) | WHSV $(hr^{-1})^a$ | Conversion to Gas (%) | $H_2$ (%) | Alkanes (%) | $CO_2$ (%) |
| RhRe | 16 | 5% | 1:1:0 | 1.73 | 100% | 52% | 20% | 28% |
| RhReCe | 19 | 5% | 1:2:2 | 1.8 | 56% | 63% | 6% | 27% |
| RhReCe | 21 | 5% | 1:1:1 | 2.0 | 95% | 63% | 8% | 31% |
| RhReLa | 22 | 5% | 1:1:3 | 0.5 | 97% | 55% | 11% | 28% |

$^a$Weight hour space velocities (WHSV) are based on feed rate of oxygenated substrate

Example 24

A Pt/Fe on carbon catalyst (Degussa CF105) was tested utilizing various concentrations of glycerol in water. This catalyst contained a loading of 5 wt % Pt and 0.5 wt % Fe. The catalyst was pretreated under flowing hydrogen at 250° C., before the liquid feed containing glycerol was introduced to the catalyst at 230° C. Table 4 shows the results of reforming the different glycerol solutions over this Pt/Fe catalyst.

TABLE 4

Activity of 5 wt % Pt/0.5 wt % Fe on Activated Carbon

| | | | | | Gas Composition | | |
|---|---|---|---|---|---|---|---|
| Wt % Glycerol | APR T(° C.) | P (PSI) | WHSV $(hr^{-1})^a$ | Conversion to Gas (%) | $H_2$ (%) | Alkanes (%) | $CO_2$ (%) |
| 10 | 230 | 433 | 1.8 | 62% | 67% | 5% | 28% |
| 20 | 230 | 428 | 3.6 | 32% | 66% | 4% | 30% |
| 30 | 230 | 431 | 5.4 | 21% | 64% | 4% | 32% |
| 40 | 235 | 429 | 7.2 | 13% | 62% | 4% | 34% |
| 50 | 238 | 432 | 9.0 | 9% | 60% | 4% | 36% |
| 60 | 237 | 431 | 10.8 | 6% | 56% | 3% | 41% |

$^a$Weight hour space velocities (WHSV) are based on feed rate of oxygenated substrate.

Example 25

PtRe Catalyst, 5% wt. Pt, 2.5:1 Molar Ratio Re:Pt

Dihydrogenhexachloroplatinate (IV) hexahydrate (Alfa Aesar 39.85% Pt) 1.18 g, and Perrhenic acid solution (Alfa Aesar 79.18% HReO$_4$) 1.92 g was diluted to 10.75 mL. The solution was added by incipient wetting to 8.95 g of hydrogen peroxide functionalized (Example 20) UU 60×120 mesh carbon and dried at 100° C. under vacuum.

Example 26

Oxidization with air has been used to functionalize activated carbons to provide improved supports for APR catalysts. Activated carbon, 23 g, was placed in a quartz U tube and heated to 450° C. in a stream of nitrogen, 150 mL/min. Once the temperature was stable, a stream of air, 50 mL/min, was added to the nitrogen. The carbon was treated for 10 hours, then allowed to cool under flowing nitrogen.

Example 27

RhReCe Catalyst, 5% wt. Rh, 1:1:1 Molar Ratio Re:Rh:Ce

Rhodium, rhenium, and ceria were added to activated carbon that has been air oxidized using the method of Example 26. An aqueous solution, 9.3 mL, containing 4.34 g of rhodium (III) nitrate solution (Alfa Aesar, 13.82% Rh), 1.85 g of perrhenic acid solution (Alfa Aesar, 79.18% HReO$_4$), 2.53 Cerium (III) nitrate was added to 11.4 g air-oxidized carbon (Calgon OLC-AW, sieved to 18-40 mesh) by incipient wetting. The mixture was dried at 100° C. under vacuum.

Example 28

PtRe Catalyst, 5% wt. Pt, 2.5:1 Molar Ratio Re:Pt)

Dihydrogenhexachloroplatinate (IV) hexahydrate (Alfa Aesar 39.85% Pt) 1.18 g, and Perrhenic acid solution (Alfa Aesar 79.18% HReO$_4$) 1.92 g was diluted to 10.75 mL. The solution was added by incipient wetting to 8.95 g of air oxidized UU 60×120 mesh carbon and dried at 100° C. under vacuum.

Example 29

RhReCe Catalyst, 5% wt. Rh, 1:1:1 Molar Ratio Re:Rh:Ce

Rhodium (III) Nitrate Dihydrate 1.37 g (Alfa Aesar 31.91% Rh), Perrhenic Acid solution (Alfa Aesar 79.18% HReO4) and Cerium (III) Nitrate Hexahydrate 1.85 g was diluted to 13.2 mL. The solution was added to 8.31 g of UU 120×200 mesh activated carbon by incipient wetting and dried at 100° C. under vacuum.

Example 30

Functionalized carbon surfaces were modified by impregnation of metal oxides prior to impregnation of catalyst precursors. Titanium n-butoxide, 1.95 g, was diluted to 12 mL with anhydrous isopropanol. This solution was added by incipient wetting to air oxidation functionalized carbon (see Example 26 above), 10 g. The wetted carbon was dried under vacuum at 100° C. overnight.

Example 31

RhReCe Catalyst, 5% wt. Rh, 1:1:1 Molar Ratio Re:Rh:Ce

Rhodium(III) Nitrate, 3.86 g, Perrhenic Acid, 1.64 g, and Cerium(III) Nitrate hexahydrate, 2.21 g, were dissolved in enough DI water to make 12 mL of solution. This solution was added by incipient wetting to Titania modified carbon from Example 30, and then dried under vacuum at 100° C. overnight.

Example 32

The catalysts of Examples 25 through 31 were pretreated under flowing hydrogen at 250° C., before the liquid feed containing oxygenated compounds were introduced to the catalyst at the desired reaction temperature. Table 5 shows the results of reforming the different solutions over these catalysts. When compared to the results for the conversion of higher concentrations of glycerol presented in Example 24, Table 5 shows that the combination of rhenium and Group VIII metals supported on activated carbon significantly enhances the activity for the reforming of higher concentrations of oxygenated compounds.

TABLE 5

Activity for APR Catalysts reforming high concentration substrates

| | | | | | Molar Ratios | | | Gas Composition | | |
|---|---|---|---|---|---|---|---|---|---|---|
| Feedstock | Catalyst | Ex. | Carbon Pretreatment | Wt % M | (Re:Rh:Ce or Re:Pt) | WHSV (hr$^{-1}$)$^a$ | Conversion to Gas (%) | H$_2$ (%) | Alkanes (%) | CO$_2$ (%) |
| 30% Ethylene Glycerol | RhReCe | 27 | Air oxided | 5% Rh | 1:1:1 | 4.8 | 47% | 61% | 10% | 29% |
| 30% Glycerol | PtRe | 25 | H$_2$O$_2$ | 5% Pt | 2.5:1 | 2.0 | 81% | 45% | 17% | 35% |
| 30% Sorbitol | PtRe | 28 | Air oxided | 5% Pt | 2.5:1 | 2.2 | 57% | 36% | 12% | 47% |
| 30% Sorbitol | RhReCe | 29 | None | 5% Rh | 1:1:1 | 2.0 | 28% | 36% | 16% | 48% |
| 50% Glycerol | PtRe | 25 | H$_2$O$_2$ | 5% Pt | 2.5:1 | 3.2 | 66% | 43% | 16% | 40% |

TABLE 5-continued

Activity for APR Catalysts reforming high concentration substrates

| | | | | | Molar Ratios | | | Gas Composition | | |
|---|---|---|---|---|---|---|---|---|---|---|
| Feedstock | Catalyst | Ex. | Carbon Pretreatment | Wt % M | (Re:Rh:Ce or Re:Pt) | WHSV $(hr^{-1})^a$ | Conversion to Gas (%) | $H_2$ (%) | Alkanes (%) | $CO_2$ (%) |
| 50% Glycerol | RhReCe | 31 | Air oxided Ti Modified | 5% Rh | 1:1:1 | 1.8 | 81% | 49% | 19% | 35% |
| 50% Sorbitol | RhReCe | 31 | Air oxided Ti Modified | 5% Rh | 1:1:1 | 1.8 | 60% | 41% | 14% | 46% |

$^a$Weight hour space velocities (WHSV) are based on feed rate of oxygenated substrate.

Example 33

Functionalized carbon surfaces were modified by impregnation of with metal oxides prior to impregnation of catalyst precursors. Vanadium oxide triisopropoxide, 0.67 g, was diluted to 12 mL with anhydrous isopropanol. This solution was added by incipient wetting to hydrogen peroxide functionalized carbon (see Example 20 above), 10 g. The wetted carbon was dried under vacuum at 100° C. overnight.

Example 34

RhReCe Catalyst, 5% wt. Rh, 1:1:1 Molar Ratio Re:Rb:Ce)

Rhodium(III) Nitrate, 3.82 g, Perrhenic Acid, 1.69 g, and Cerium(III) Nitrate hexahydrate, 2.21 g, were dissolved in enough DI water to make 12 mL of solution. This solution was added by incipient wetting to Vanadia modified carbon, and then dried under vacuum at 100° C. overnight.

Example 35

The catalysts of Examples 29, 31 and 34 were pretreated under flowing hydrogen at 250° C., before the liquid feed containing oxygenated compounds were introduced to the catalyst at the desired reaction temperature. Table 6 shows the results of reforming 30 wt % sorbitol at 240° C. and 495 psig. This table shows that addition of either Ti or V significantly improves the conversion of sorbitol.

TABLE 6

Activity for APR Catalysts 30% Sorbitol supported on modified carbons.

| | | | | | | | Gas Composition | | |
|---|---|---|---|---|---|---|---|---|---|
| Catalyst | Ex. | Carbon Pretreatment | Wt % M | Molar Ratios (Re:Rh:Ce) | WHSV $(hr^{-1})^a$ | Conversion to Gas (%) | $H_2$ (%) | Alkanes (%) | $CO_2$ (%) |
| RhReCe | 29 | None | 5% Rh | 1:1:1 | 2.0 | 28% | 36% | 16% | 48% |
| RhReCe | 31 | Air oxided Ti Modified | 5% Rh | 1:1:1 | 1.8 | 72% | 51% | 11% | 40% |
| RhReCe | 34 | $H_2O_2$ V Modified | 5% Rh | 1:1:1 | 1.8 | 83% | 47% | 12% | 42% |

$^a$Weight hour space velocities (WHSV) are based on feed rate of oxygenated substrate.

Example 36

It has been found that the addition of bases significantly increases the amount of hydrogen generated during aqueous-phase reforming. Table 7 shows the effects of adding various amounts of NaOH and KOH.

TABLE 7

Effect of Addition of Base to Feed on Activity and Selectivity for APR Catalysts.

| | | | | | Molar Ratios | | | Gas Composition | | |
|---|---|---|---|---|---|---|---|---|---|---|
| Feedstock | Catalyst | Ex. | Base | Wt % M | (Re:Rh:Ce or Re:Pt) | WHSV $(hr^{-1})^a$ | Conversion to Gas (%) | $H_2$ (%) | Alkanes (%) | $CO_2$ (%) |
| 30% Sorbitol | RhReCe | $NA^b$ | none | 5% Rh | 1:1:1 | 1.8 | 70% | 47% | 12% | 40% |
| 30% Sorbitol | RhReCe | b | 0.5% NaOH | 5% Rh | 1:1:1 | 1.7 | 71% | 53% | 8% | 39% |
| 30% Sorbitol | RhReCe | b | 1.25% NaOH | 5% Rh | 1:1:1 | 1.8 | 78% | 57% | 8% | 37% |
| 30% Sorbitol | RhReCe | b | 1.5% NaOH | 5% Rh | 1:1:1 | 1.8 | 75% | 56% | 8% | 34% |

TABLE 7-continued

Effect of Addition of Base to Feed on Activity and Selectivity for APR Catalysts.

| Feedstock | Catalyst | Ex. | Base | Wt % M | Molar Ratios (Re:Rh:Ce or Re:Pt) | WHSV $(hr^{-1})^a$ | Conversion to Gas (%) | $H_2$ (%) | Alkanes (%) | $CO_2$ (%) |
|---|---|---|---|---|---|---|---|---|---|---|
| 30% Sorbitol | RhReCe | b | 1.65% NaOH | 5% Rh | 1:1:1 | 1.8 | 73% | 56% | 8% | 34% |
| 30% Sorbitol | PtRe | 28 | none | 5% Pt | 2.5:1 | 2.2 | 57% | 36% | 12% | 47% |
| 30% Sorbitol | PtRe | 28 | 2.5% KOH | 5% Pt | 2.5:1 | 2.2 | 64% | 55% | 7% | 36% |
| 50% Sorbitol | RhReCe | 31 | none | 5% Rh | 1:1:1 | 1.8 | 81% | 49% | 19% | 35% |
| 50% Sorbitol | RhReCe | 31 | 1.65% NaOH | 5% Rh | 1:1:1 | 1.8 | 75% | 57% | 12% | 33% |

$^a$Weight hour space velocities (WHSV) are based on feed rate of oxygenated substrate.
$^b$preparation of this catalyst (on $H_2O_2$ vanadium modified carbon) was not described in any example, but the procedure was similar to example 34.

Example 37

A 3 wt % platinum catalyst supported on activated carbon was prepared according to the general method of Example 1. An aqueous solution, approximately 9.5 mL, containing 0.75 g of dihydrogen hexachloroplatinate (IV) hexahydrate (Alfa Aesar, 39.85% Pt) and 1.22 g of perrhenic acid solution (Alfa Aesar, 79.18% $HReO_4$) was added to 10.0 g peroxide functionalized carbon (Calgon UU, sieved to 60-120 mesh functionalized using the method of Example 20). The mixture was dried at 100° C. under vacuum.

Example 38

Figure 5:
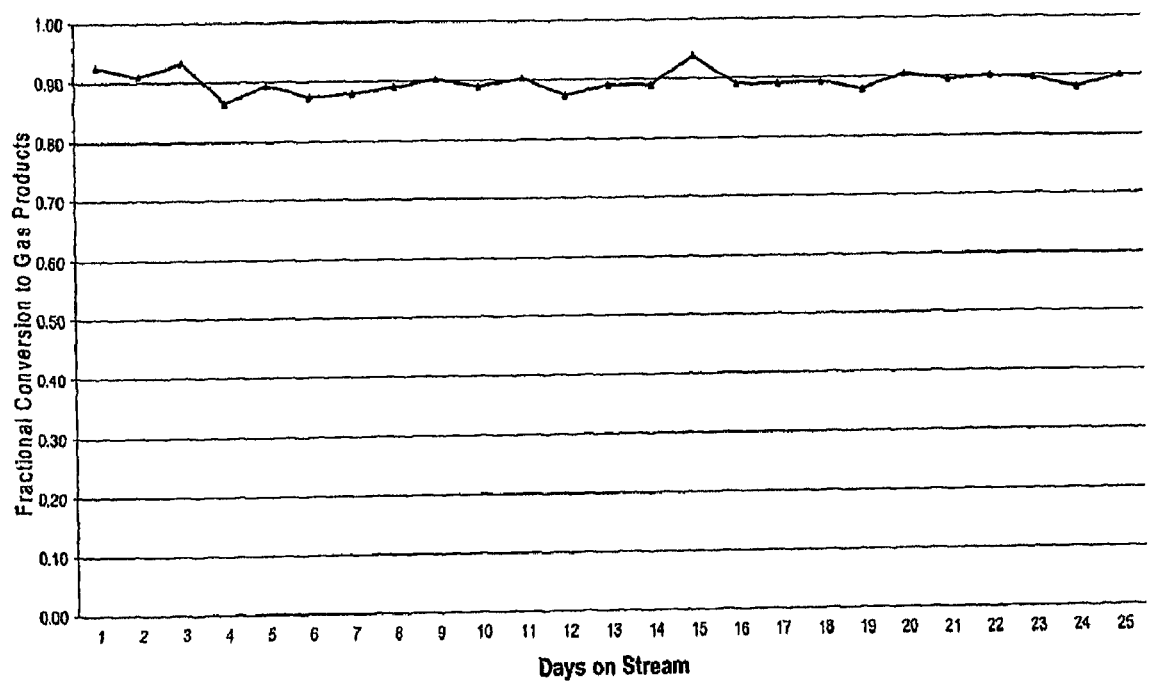
FIG. 5 is a graph depicting the conversion of Glycerol to Gas Phase Products using aqueous phase reforming according to one embodiment of the present invention.

The catalysts of Example 37 was pretreated under flowing hydrogen at 350° C., before the liquid feed containing oxygenated compounds were introduced to the catalyst at the desired reaction temperature. FIG. 5 shows the time-dependent results of fractional conversion to gas for reforming 50 wt % glycerol at 260° C., 600 psig and a WHSV of 0.55 based on the feed rate of glycerol.

Example 39

ReRh Bimetallic Catalyst, 5% wt. Rh, 1:2 Molar Ratio Re:Rh

An aqueous solution, 7.6 mL, containing 0.85 g of perrhenic acid solution (Alfa Aesar 76.41% $HReO_4$) was added to 10.0 g of 5% wt Rh catalyst, Example 4, by incipient wetting. The mixture was dried at 100° C. under vacuum.

Example 40

ReRh Bimetallic Catalyst, 5% wt. Rh, 1:1 Molar Ratio Re:Rh

An aqueous solution, 7.6 mL, containing 1.61 g of perrhenic acid solution (Alfa Aesar 76.41% $HReO_4$) was added to 10.0 g of 5% wt Rh catalyst, Example 4, by incipient wetting. The mixture was dried at 100° C. under vacuum.

Example 41

ReRh Bimetallic Catalyst, 5% wt. Rh, 1:1 Molar Ratio Re:Rh

An aqueous solution, 15 mL, containing 3.15 g of rhodium (III) nitrate (Alfa Aesar) was added to 19.0 g activated carbon (Calgon OLC-AW, sieved to 18-40 mesh) by incipient wetting. The mixture was dried at 100° C. under vacuum. An additional application of aqueous solution, 15.2 mL, containing 3.14 g of perrhenic acid solution (Alfa Aesar 79.2% $HReO_4$) performed. The mixture was dried at 100° C. under vacuum.

Example 42

ReRh Bimetallic Catalyst, 5% wt. Rh, 2:1 Molar Ratio Re:Rh

An aqueous solution, 7.6 mL, containing 1.57 g of rhodium (III) nitrate (Alfa Aesar) and 3.11 g of perrhenic acid solution (Alfa Aesar 76.41% $HReO_4$) was added to 9.53 g activated carbon (Calgon OLC-AW, sieved to 18-40 mesh) by incipient wetting. The mixture was dried at 100° C. under vacuum.

Example 43

It has been found that increasing the rhenium loading will enhance the production of alkane products. Table 8 shows the results of reforming two concentrations of ethylene glycol over catalysts with varying ratios of Re to Rh. As this ratio increased, the concentration of alkanes in the product gas increased.

TABLE 8

Effect of increasing Re:Rh ratio on Activity and Selectivity for APR Catalysts.

| Feedstock | Catalyst | Ex. | T (° C.) | Wt % Rh | Molar Ratios (Re:Rh) | WHSV $(hr^{-1})^a$ | Conversion to Gas (%) | $H_2$ (%) | Alkanes (%) | $CO_2$ (%) |
|---|---|---|---|---|---|---|---|---|---|---|
| 10% Ethylene Glycol | RhRe | 15 | 210 | 5% | 1:3.8 | 0.8 | 36% | 65% | 7% | 27% |

TABLE 8-continued

Effect of increasing Re:Rh ratio on Activity and Selectivity for APR Catalysts.

| Feedstock | Catalyst | Ex. | T (° C.) | Wt % Rh | Molar Ratios (Re:Rh) | WHSV (hr$^{-1}$)$^a$ | Conversion to Gas (%) | Gas Composition | | |
|---|---|---|---|---|---|---|---|---|---|---|
| | | | | | | | | H$_2$ (%) | Alkanes (%) | CO$_2$ (%) |
| 10% Ethylene Glycol | RhRe | 39 | 210 | 5% | 1:2 | 0.7 | 89% | 59% | 12% | 29% |
| 10% Ethylene Glycol | RhRe | 40 | 210 | 5% | 1:1 | 0.7 | 100% | 48% | 24% | 27% |
| 30% Ethylene Glycol | RhRe | 41 | 230 | 5% | 1:1 | 2.2 | 19% | 60% | 10% | 28% |
| 30% Ethylene Glycol | RhRe | 42 | 230 | 5% | 2:1 | 2.1 | 20% | 53% | 17% | 30% |

$^a$Weight hour space velocities (WHSV) are based on feed rate of oxygenated substrate.

The described embodiments and examples are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A method of reforming oxygenated hydrocarbons in a feedstock solution, the method comprising the steps of
    modifying an aqueous-stable support comprising carbon with a member selected from the group consisting of titanium, vanadium and tungsten, and
    contacting the feedstock solution with a reforming catalyst on the modified support under conditions of reaction temperature and reaction pressure effective to produce hydrogen gas and alkanes having 1 to 8 carbon atoms,
    wherein the feedstock solution comprises oxygenated hydrocarbons in an amount of at least 20 weight percent and
    wherein the reforming catalyst comprises rhenium and at least one Group VIII transition metal.

2. The method of claim 1, wherein the conversion to hydrogen gas is greater with the reforming catalyst than the conversion to hydrogen gas using the same feedstock solution and the same catalyst absent rhenium.

3. The method of claim 1, wherein the conversion to alkanes with the reforming catalyst is greater than the conversion to alkanes using the same feedstock solution and the same catalyst absent rhenium.

4. The method of claim 1, wherein the support comprises activated carbon, and wherein the combination of rhenium and the at least one Group VIII transition metal on the activated carbon significantly enhances the activity for reforming the oxygenated hydrocarbon compared to a monometallic catalyst comprising Pt, Ru, Rh, Re, Pd, Ir or Ni.

5. The method of claim 1, wherein the aqueous-stable support comprises activated carbon, and wherein the combination of rhenium and the at least one Group VIII transition metal on the activated carbon significantly enhances the activity for reforming the oxygenated hydrocarbon compared to a Pt/Fe on carbon catalyst.

6. The method of any one of claims 1-5, wherein the reforming catalyst comprises Re and at least one transition metal selected from the group consisting of: Ir, Ni, Pd, Pt, Rh and Ru.

7. The method of any one of claims 1-5, wherein the reforming catalyst further comprises Ce or La.

8. The method of any one of claims 1-5, wherein the aqueous-stable support comprises one or more materials selected from the group consisting of:
    carbon, zirconia, titania, ceria and combinations thereof.

9. The method of any one of claims 1-5, wherein the atomic ratio of Re to the Group VIII metal in the catalyst is from 0.25-to-1 to 10-to-1, and the combination of the catalyst and the support comprises from 0.25 wt % to 10 wt % Group VIII metal.

10. The method of any one of claims 1-5, wherein the catalyst is selected from the group consisting of: Re$_{1.0}$Rh$_{3.8}$, Re$_{1.0}$Rh$_{1.0}$, Ni$_{1.0}$Re$_{16.0}$, Re$_{1.0}$Rh$_{2.0}$Ce$_{2.0}$, Re$_{1.0}$Rh$_{1.0}$Ce$_{1.0}$, Re$_{1.0}$Rh$_{1.0}$La$_{3.0}$, and Re$_{2.5}$Pt$_{1.0}$.

11. The method of any one of claims 1-5, wherein the feedstock solution comprises at least 50% of the oxygenated compound.

12. The method of any one of claims 1-5, wherein the reaction temperature is between about 80° C. and about 300° C. and wherein the reaction pressure is between about 10 bar (145 psi) and about 50 bar (725 psi).

13. A reforming catalyst prepared by a process comprising the steps of:
    (a) impregnating a carbon support with titania, vanadia, tungsten or zirconia;
    (b) adhering a catalytic composition to the impregnated carbon support, the catalytic composition comprising Re and a second metal selected from the group consisting of: Ir, Ni, Pd, Pt, Rh and Ru; and
    (c) adhering a third metal of Ce or La to the impregnated carbon support or to the catalytic composition.

14. The reforming-catalyst of claim 13, wherein the catalytic composition is selected from the group consisting of: Re$_{1.0}$Rh$_{3.8}$, Ni$_{1.0}$Re$_{16.0}$, Re$_{1.0}$Rh$_{2.0}$Ce$_{2.0}$, Re$_{1.0}$Rh$_{1.0}$Ce$_{1.0}$, Re$_{1.0}$Rh$_{1.0}$La$_{3.0}$, and Re$_{2.5}$Pt$_{1.0}$.

15. A composition of matter comprising
    (a) a reforming catalyst comprising rhenium, a Group VIII metal, and Ce or La in which a reforming catalyst is adhered to the modified carbon support, wherein the carbon support has been modified with a member selected from the group consisting of titanium, vanadium and tungsten;
    (b) a gaseous phase comprising hydrogen, methane, carbon dioxide and one or more compounds selected from the group consisting of: ethane and propane; and (c) a liquid phase comprising a $C_1$-$C_6$ oxygenated hydrocarbon.

16. The composition of claim 15, wherein the liquid phase comprises an organic phase comprising hexane, pentane and propane and an aqueous phase comprising sorbitol.

17. The composition of claim 15 or 16, wherein the liquid phase comprises an organic phase comprising propane and an aqueous phase comprising glycerol.

18. The composition of any one of claim 15 or 16, wherein the Group VIII metal comprises one or more materials selected from the group consisting of: Ir, Ni, Pd, Pt, Rh and Ru.

\* \* \* \* \*